(12) United States Patent
Matsuoka et al.

(10) Patent No.: US 8,702,937 B2
(45) Date of Patent: Apr. 22, 2014

(54) GAS SENSOR CONTROL APPARATUS CONTROLLING OUTPUT CHARACTERISTIC OF GAS SENSOR

(75) Inventors: Mikiyasu Matsuoka, Kariya (JP); Yasuhiro Kawakatsu, Kariya (JP); Shingo Nakata, Kariya (JP); Takao Mishima, Aichi-ken (JP)

(73) Assignee: Denso Corporation, Kariya (JP)

( * ) Notice: Subject to any disclaimer, the term of this patent is extended or adjusted under 35 U.S.C. 154(b) by 297 days.

(21) Appl. No.: 13/212,438

(22) Filed: Aug. 18, 2011

(65) Prior Publication Data
US 2012/0043205 A1    Feb. 23, 2012

(30) Foreign Application Priority Data

Aug. 19, 2010  (JP) ................................. 2010-184372
May 25, 2011  (JP) ................................. 2011-117453

(51) Int. Cl.
*G01N 27/41*    (2006.01)
*G01N 27/409*   (2006.01)
*F01N 11/00*    (2006.01)
*F01N 9/00*     (2006.01)

(52) U.S. Cl.
USPC ........... 204/424; 204/406; 204/425; 204/410; 73/23.31; 73/23.32; 60/276

(58) Field of Classification Search
USPC ................. 204/421–429, 406, 410; 73/23.31, 73/23.32; 205/775–794.5; 60/276
See application file for complete search history.

(56) References Cited

U.S. PATENT DOCUMENTS

| 4,741,817 A | 5/1988 | Croset et al. |
| 2008/0060939 A1* | 3/2008 | Inoue et al. .................. 204/401 |
| 2008/0185289 A1* | 8/2008 | Matsuoka et al. ............ 204/425 |

FOREIGN PATENT DOCUMENTS

| JP | S61-118653 | 6/1986 |
| JP | 3-258947   | 11/1991 |
| JP | 8-20414    | 3/1996 |
| JP | 2007-023917 | 2/2007 |

OTHER PUBLICATIONS

Japanese Office Action dated Jul. 10, 2012 issued in corresponding Japanese Application No. 2011-117453 with English translation.

* cited by examiner

*Primary Examiner* — Jennifer Dieterle
(74) *Attorney, Agent, or Firm* — Nixon & Vanderhye PC

(57) ABSTRACT

A gas sensor control apparatus is provided which controls an operation of a gas sensor made up of a solid electrolyte body and a pair of electrodes to output a signal indicating the concentration of a given gas component contained in gas. The gas sensor control apparatus includes a constant current circuit that is connected electrically to one of the electrodes of the gas sensor and supplies a constant current thereto and a controller. The controller supplies a constant current to the gas sensor so that it flows from one of the electrodes to the other in a selected direction, thereby changing a response time the gas sensor takes to react to a change in concentration of the gas component. This results in an increased accuracy, for example, in controlling an air-fuel ratio of a mixture to an internal combustion engine in an engine control system.

3 Claims, 12 Drawing Sheets

EXCESS AIR RATIO λ

RICH-TO-LEAN

LEAN-TO-RICH

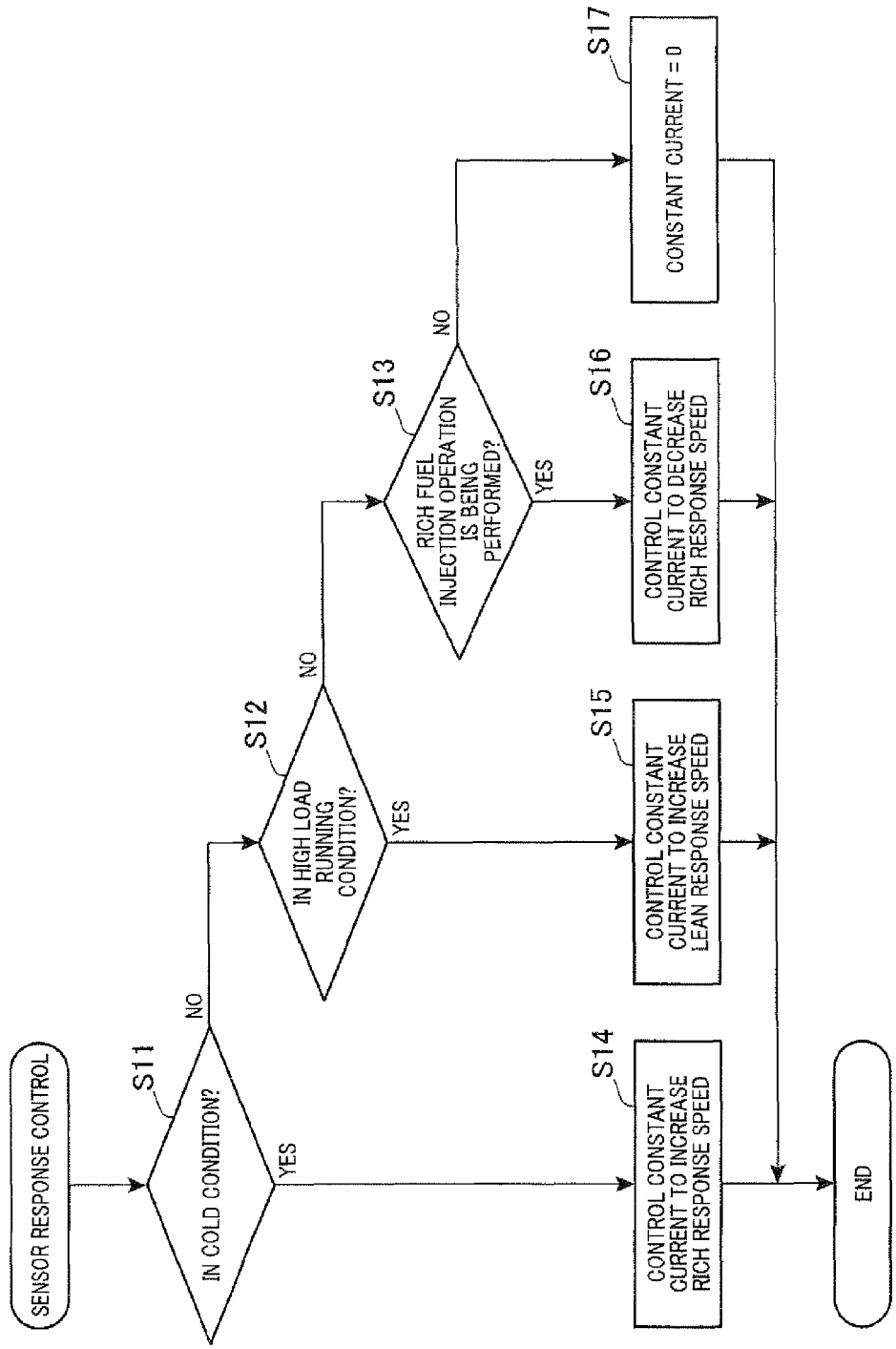

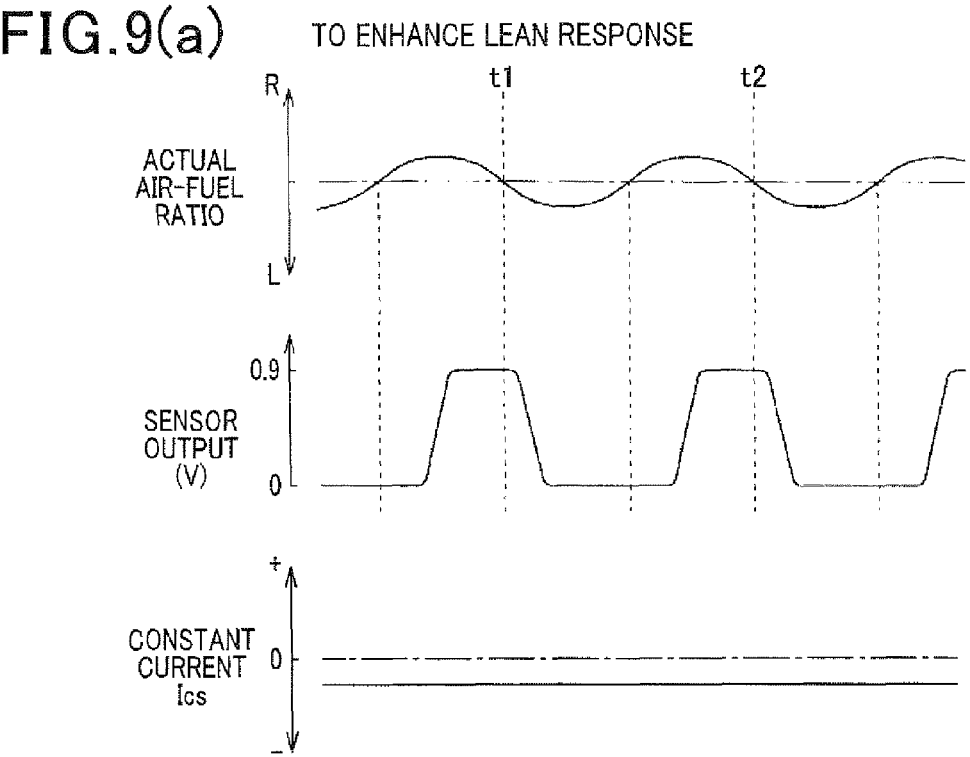
FIG.9(a) TO ENHANCE LEAN RESPONSE
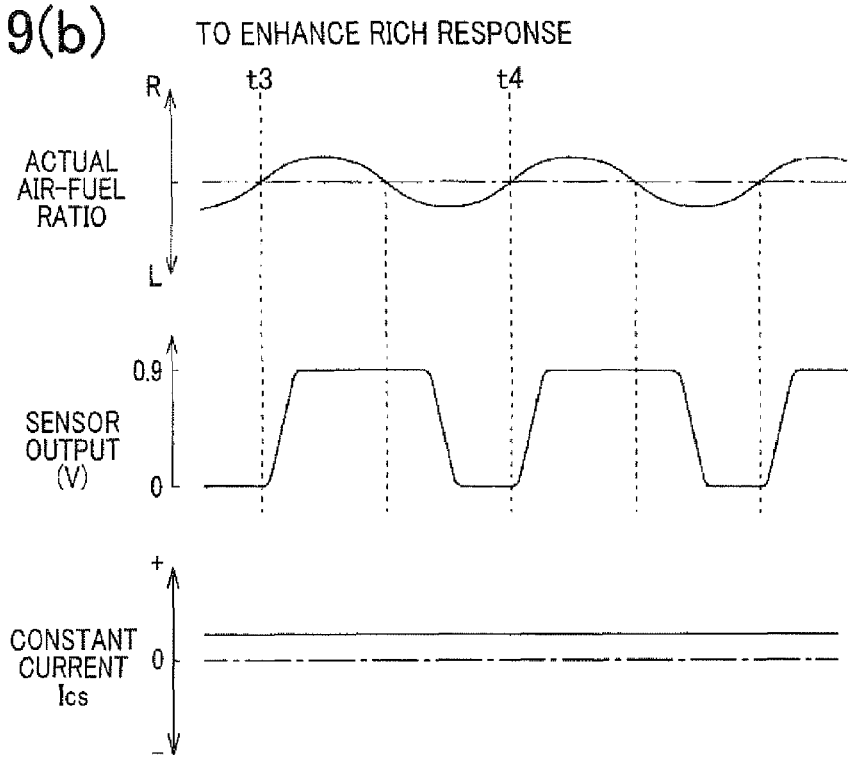
FIG.9(b) TO ENHANCE RICH RESPONSE

GAS SENSOR CONTROL APPARATUS CONTROLLING OUTPUT CHARACTERISTIC OF GAS SENSOR

CROSS REFERENCE TO RELATED DOCUMENT

The present application claims the benefits of priority of Japanese Patent Application No. 2010-184372 filed on Aug. 19, 2010 and Japanese Patent Application No. 2011-117453 filed May 25, 2011, disclosures of which are incorporated herein by reference.

BACKGROUND

1. Technical Field

The present application relates generally to a gas sensor control apparatus designed to change an output characteristic such as a response time of a gas sensor as needed.

2. Background Art

Gas sensors are known which measure the concentration of oxygen contained in exhaust gas from an automotive engine as representing an air-fuel ratio of a mixture supplied to the engine. For example, typical electromotive force $O_2$ sensors work to output an electric signal which is different in level between when the exhaust gas is rich in fuel and when the exhaust gas is lean in fuel. Specifically, such a type of $O_2$ sensors produces about 0.9V when an air-fuel ratio of the exhaust gas is in a rich state and about 0V when the air-fuel ratio is in a lean state.

The typical gas sensors usually experience a time lag in reacting to an actual change in air-fuel ratio of the exhaust gas to produce the output. The improvement of the time lag has been sought.

For example, Japanese Patent Second Publication No. 8-20414 discloses the electromotive force $O_2$ sensor equipped with an auxiliary electrochemical cell. The auxiliary electrochemical cell is connected to one of electrodes of the $O_2$ sensor. The electric current is applied to the auxiliary electrochemical cell to perform the so-called ion pumping, thereby changing the concentration of gas to be measured, that is, a λ characteristic (i.e., an electromotive force characteristic) in relation to the applied current.

The production of the electromotive force $O_2$ sensor of the above publication requires modifying the structure of a typical $O_2$ sensor greatly, thus resulting in an increase in production cost thereof.

SUMMARY

It is therefore an object to provide a simplified structure of a gas sensor control apparatus designed to change an output characteristic of a gas sensor such as a response time as needed.

According to one aspect of an embodiment, there is provided a gas sensor control apparatus which controls an operation of a gas sensor made up of a solid electrolyte body and a pair of electrodes affixed to a surface of solid electrolyte body to output a signal indicating the concentration of a given gas component contained in gas. The gas sensor control apparatus comprises: (a) a constant current circuit that is connected electrically to one of the electrodes of the gas sensor and supplies a constant current to the one of the electrodes; and (b) a controller that determines whether a change request to change an output characteristic of the gas sensor including a response time the gas sensor takes to react to a change in concentration of the gas component is made or not. When the change request is determined to be made, the controller determines the direction in which the constant current is to flow between the electrodes of the gas sensor based on the change request and controls the constant current circuit to supply the constant current to the gas sensor so that the constant current flows between the electrodes in the determined direction to change the output characteristic of the gas sensor.

When the gas component has changed in concentration or composition thereof, some components contained in the gas immediately before such changing may remain residing around the gas sensor, which results in a delay in change in level of the output of the gas sensor in response to the change in concentration or composition of the gas component ((i.e., a lag of response time of the gas sensor). How to rectify such a response time lag is thought of as being dependent on other factors.

The controller of the gas sensor control apparatus, as described above determines whether the gas sensor control apparatus is in the condition where the output characteristic of the gas sensor is to be changed or not, in other words, whether the change request is made or not. The controller determines the direction in which the constant current is to be applied between the electrodes of the gas sensor based on the change request and controls the constant current circuit to supply the constant current to the gas sensor, thereby accelerating or decelerating the removal of a component(s) of the gas other then the given component to be measured in concentration thereof upon the change in concentration of the gas component. In other words the controller is operable to change the output characteristic of the gas sensor to a desired value. Additionally, when the concentration of the gas component is not being changed, the controller is operable to accelerate or decelerate the removal of a component(s) of the gas which is different from the given component to be measured, in other words, which disturbs the measurement of the concentration of the gas component in order to change the output characteristic (e.g., the value of and output) of the gas sensor. The changing of the output characteristic of the gas sensor is accomplished with the constant current circuit, thus eliminating the need for changing the structure of the gas sensor and for a complicated structure of the gas sensor control apparatus.

In the preferred mode of the embodiment, the gas sensor is designed to measure an air-fuel ratio of exhausts gas emitted from an internal combustion engine as a function of the concentration of the gas component and outputs the signal indicative of the air-fuel ratio. The change request is to change the output characteristic of the gas sensor at at least one of times when the air-fuel ratio of the exhaust gas changes from rich to lean and when the air-fuel ratio of the exhaust gas changes from lean to rich. The controller determines the direction in which the constant current is to be applied to flow between the electrodes of the gas sensor based on the change request to change the output characteristic at the at least one of the times when the air-fuel ratio of the exhaust gas changes from rich to lean and when the air-fuel ratio of the exhaust gas changes from lean to rich.

Usually, the air-fuel ratio of the exhaust gas emitted from the internal combustion engine changes between a rich state and a lean state. When the air-fuel ratio changes from the rich to lean state, rich components of the exhaust gas such as HC components stay around the gas sensor, which will disturb the reaction of lean components such as NOx components on the electrodes of the gas sensor. This results in a decrease in responsivity of the gas sensor to the change in the air-fuel ratio to the lean side.

In order to alleviate the above drawback, the controller decides whether the output of the gas sensor is to be changed upon a change in air-fuel ratio to the lean state or the rich state and determines the direction in which the constant current is to be applied to flow between the electrodes of the gas sensor based on a result of the decision. The constant current circuit applied the constant current to the gas sensor in the determined direction, thereby changing the output characteristic to a desired value.

The gas sensor has defined therein a reference gas chamber filled with a reference gas. The electrodes of the gas sensor serve as an exhaust gas-exposed electrode exposed to the exhaust gas and a reference gas-exposed electrode exposed to the reference gas, respectively. When the change request is determined to be made to change the response time of the gas sensor when the air-fuel ratio of the exhaust gas changes from rich to lean, the controller controls the constant current circuit to orient the direction of flow of the constant current so that oxygen is supplied from the reference gas-exposed electrode to the exhaust gas-exposed electrode through the solid electrolyte body. When the change request is determined to be made to change the response time of the gas sensor when the air-fuel ratio of the exhaust gas changes from lean to rich, the controller controls the constant current circuit to orient the direction of flow of the constant current so that oxygen is supplied from the exhaust gas-exposed electrode to the reference gas-exposed electrode through the solid electrolyte body.

Specifically, when the air-fuel ratio changes from rich to lean, the constant current circuit applies the constant current, so that the oxygen is moved from the reference gas-exposed electrode to the exhaust gas-exposed electrode through the solid electrolyte body, thereby accelerating the removal of the rich components such as HC components residing around the exhaust gas-exposed electrode to enhance the response time of the gas sensor upon a change in air-fuel ratio to the lean state. When the air-fuel ratio changes from lean to rich, the constant current circuit applies the constant current, so that the oxygen is moved from the exhaust gas-exposed electrode to the reference gas-exposed electrode through the solid electrolyte body, thereby accelerating the removal of the lean components such as NOx components residing around the exhaust gas-exposed electrode to enhance the response time of the gas sensor upon a change in air-fuel ratio to the rich state.

The controller may also determine an operating condition of the internal combustion engine and decide whether the change request is made or not based on the determined operating condition of the internal combustion engine.

Usually, the output characteristic of the gas sensor changes with a change in operating condition of the internal combustion engine. The determination of whether the change request is made or not is preferably made based on the operating condition of the internal combustion engine.

The gas sensor control apparatus may be used with an engine control system which brings the air-fuel ratio into agreement with a target value. The controller determines that the change request is made to shorten the response time of the gas sensor upon a change in the air-fuel ratio from rich to lean when the operating condition indicates that the internal combustion engine is in a high load condition and controls the constant current circuit based on the change request to decrease the response time of the gas sensor.

When the internal combustion engine is running in the high load condition, the amount of fresh air sucked into the internal combustion engine becomes great, so that an emitted quantity of the lean components (i.e., the HOx components) is increased. The controller enhances the response time of the gas sensor upon the change in air-fuel ratio to the lean side, thereby ensuring the accuracy in output from the gas sensor, which enables the engine control system to minimize the emitted quantity of the lean components.

In the case where the gas sensor control apparatus is used with the engine control system which brings the air-fuel ratio into agreement with the target value, the controller may also determine that the change request is made to shorten the response time of the gas sensor upon a change in the air-fuel ratio from lean to rich when the operating condition indicates that the internal combustion engine is in a cold condition and controls the constant current circuit based on the change request to decrease the response time of the gas sensor.

When the internal combustion engine is running in the cold condition, the engine control system increases the quantity of fuel to be burned in a combustion chamber of the internal combustion engine, so that the quantity of the rich components (i.e., the HC components) to be emitted increases. The controller enhances the response time of the gas sensor upon the change in air-fuel ratio to the rich side, thereby ensuring the accuracy in output from the gas sensor, which enables the engine control system to minimize the emitted quantity of the rich components.

The controller may increase or lengthen the response time of the gas sensor as needed.

For example, the gas sensor control apparatus may be employed in an engine control system which includes an upstream catalyst disposed in an exhaust pipe extending from the internal combustion engine, a downstream catalyst disposed in a portion of the exhaust pipe which is located downstream of the upstream catalyst, and the gas sensor installed between the upstream catalyst and the downstream catalyst. The engine control system works to cut the fuel to be supplied to the internal combustion engine during running of the internal combustion engine and also perform a rich fuel injection operation based on the air-fuel ratio of the exhaust gas, as determined based on the output from the gas sensor, to eliminate an excess oxygen condition (i.e., an extremely lean state) of the upstream and downstream catalysts upon the completion of the fuel cut to the internal combustion engine. The controller decides that the change request is made to increase the response time of the gas sensor upon a change in air-fuel ratio to the rich side when the rich fuel injection operation is performed. The constant current circuit supplies the constant current to the gas sensor to lengthen the response time of the gas sensor upon the change in air-fuel ratio to the rich side.

Specifically, when the engine control system cuts the fuel to the internal combustion engine, it will cause the upstream and downstream catalysts to be placed in the excess oxygen condition (i.e., the extremely lean state). In order to eliminate the excess oxygen condition of the upstream and downstream catalysts, in other words, place the upstream and downstream catalysts in a neutral condition where a proper quantity of oxygen stays in the upstream and downstream catalysts quickly immediately after the completion of the fuel cut to the internal combustion engine, the engine control system performs the rich fuel injection operation based on the air-fuel ratio of the exhaust gas. The gas sensor is disposed intermediate between the upstream and downstream catalysts. The engine control system determines whether the air-fuel ratio of the exhaust gas has changed from the lean side to the rich state based on the output from the gas sensor and then terminates the rich fuel injection operation when it is determined that the air-fuel ratio has changed to the rich state. However, at a moment when the air-fuel ratio of the exhaust gas has changed from the lean state to the rich state at the location of the gas sensor, the upstream catalyst may have already been neutralized, but the downstream catalyst may be still placed in the excess oxygen condition.

The gas sensor control apparatus is operable to increase the response time of the gas sensor upon the change in air-fuel ratio to the rich state when the rich fuel injection operation is performed. Specifically, a lag in response of the gas sensor to an actual change in air-fuel ratio of the exhaust gas from the lean state to the rich state during the rich fuel injection operation is created. This enables the engine control system to terminate the rich fuel injection operation with a delay after the upstream catalyst is neutralized, thereby neutralizing the upstream and downstream catalysts properly and ensuring the stability in controlling exhaust emissions immediately after the completion of the fuel cut to the engine.

The constant current circuit may be designed to regulate an amount of the constant current which is to be applied to the gas sensor. The controller determines a target amount of the constant current required to be applied to the gas sensor to change a degree of the response time of the gas sensor based on the change request. Specifically, when it is required to regulate the response time of the gas sensor to be different between when the air-fuel ratio changes to the rich state and when to the lean state, the controller determines the target amount of the constant current to be supplied to the gas sensor as required to change the degree of the response time to a desired value.

When the internal combustion engine is running in a transient period of time in which a load on the internal combustion engine is increasing or in a high load steady state period of time in which the load on the internal combustion engine stops increasing, so that the internal combustion engine is in a high load condition, the controller determines that the change request is made to shorten the response time of the gas sensor upon a change in the air-fuel ratio from rich to lean and changes a degree of the response time of the gas sensor in the transient period of time to be shorter than that in the high load steady state period of time.

Specifically, the period of time in which the engine is running in the high load condition includes the transient period of time in which the load on the engine is increasing and the high load steady state period of time in which the load on the engine stops increasing, and the engine is kept running in the high load condition. In either of the transient period of time or the high load steady state period of time, the quantity of fresh air inducted into the engine usually becomes great, so that the lean components such as the NOx components increase. It is, therefore, advisable that the response time of the gas sensor upon a change in air-fuel ratio to the lean state be shortened in order to decrease an emitted amount of the lean components. However, there is fear that the emitted amount of the lean components increase greatly in the transient period of time as compared with the high load steady state period of time. The controller, thus, changes the response time of the gas sensor upon a change in the air-fuel ratio from rich to lean in the transient period of time to be shorter than that in the high load steady state period of time. This ensures a balance in emitting the lean components between the transient period of time and the high load steady state period of time.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 8 is a flowchart of a response control program to be executed by the gas sensor control apparatus of FIG. 1 to change the response time of the $O_2$ sensor of FIG. 2;

FIG. 9(a) is a time chart which demonstrates a relation among an actual air-fuel ratio of exhaust gas, an output of the $O_2$ sensor of FIG. 2, and a constant current applied to the $O_2$ sensor when the response time of the $O_2$ sensor upon a change in air-fuel ration from rich to lean is enhanced;

FIG. 9(b) is a time chart which demonstrates a relation among an actual air-fuel ratio of exhaust gas, an output of the $O_2$ sensor of FIG. 2, and a constant current applied to the $O_2$ sensor when the response time of the $O_2$ sensor upon a change in air-fuel ration from lean to rich is enhanced;

DESCRIPTION OF THE PREFERRED EMBODIMENTS

Figure 1:
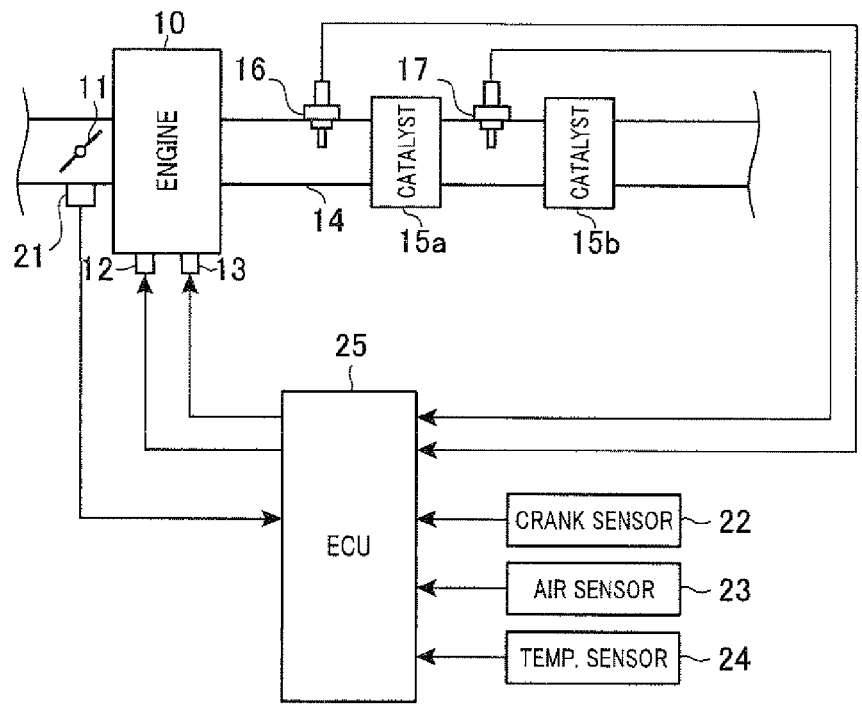
FIG. 1 is a block diagram which illustrates an engine control system equipped with a gas control apparatus according to the first embodiment of the invention.

Referring to the drawings, wherein like reference numbers refer to like parts in several views, particularly to FIG. 1, there is shown an engine control system according to the first embodiment which is designed to monitor outputs of gas sensors installed in an exhaust pipe of an internal combustion engine mounted in an automotive vehicle to perform some engine control tasks. The engine control system is equipped with a gas sensor control apparatus and includes an electronic control unit (ECU) 25 to control the quantity of fuel to be sprayed into an internal combustion engine 10 (e.g., an air-fuel ratio of a mixture to be supplied to the engine 10), the ignition timing of the fuel, etc.

The engine 10 is a gasoline engine and equipped with an electronically-controlled throttle valve 11, fuel injectors 12 (only one is shown for the brevity of illustration), and an ignition device (i.e., an igniter) 13. The exhaust pipe 14 extending from the engine 10 has installed therein catalytic converters 15a and 15b working as an exhaust emission control device. Each of the catalytic converters 15a and 15b includes three-way catalyst. The catalytic converter 15a serves as a first catalyst (which will also be referred to as an upstream catalyst) located upstream of the exhaust pipe 14, while the catalytic converter 15b serves as a second catalyst (which will also be referred to as a downstream catalyst) installed in a portion of the exhaust pipe 14 which is located downstream of the first catalyst 15a. The catalytic converters 15a and 15b will also be referred to as the first and second catalyst 15a and 15b below, respectively. The engine control system also includes an air-fuel ratio (A/F) sensor 16 and an $O_2$ sensor 17. The A/F sensor 16 is installed in a portion of the exhaust pipe 14 which is located upstream of the first catalyst 15a. The $O_2$ sensor 17 is disposed between the first and second catalysts 15a and 15b, that is, upstream of the second catalyst 15b and downstream of the first catalyst 15a. The A/F sensor 16 works to output an electrical signal which is substantially proportional in level to an air-fuel ratio of exhaust gas flowing through the exhaust pipe 14. Note that the air-fuel ratio of the mixture is proportional to the concentration of oxygen in the exhaust gas and thus is usually referred to as the air-fuel ratio of the exhaust gas in the field of engine control. The $O_2$ sensor 17 works to output an electrical signal in the form of an electromotive force which is different in level between when the air-fuel ratio of the exhaust gas is in the rich state and when the air-fuel ratio is in the lean state.

The engine control system also includes a throttle position sensor 21, a crank angle sensor 22, an intake air flow sensor 23, and a coolant temperature sensor 24. The throttle position sensor 21 measures the position of a throttle valve 11 which represents the degree to which the throttle valve 11 is opened. The crank angle sensor 22 outputs a rectangular signal (i.e., a pulse signal), for example, every 30° of rotation of a crankshaft of the engine 10. The intake air flow sensor 23 measures the flow rate of intake air to be sucked into the engine 10. The coolant temperature sensor 24 measures the temperature the coolant of the engine 10. The engine control system also includes a combustion pressure sensor, an accelerator position sensor, an oil temperature sensor, etc. which are all not shown. The combustion pressure sensor measures the pressure in a combustion chamber of the engine 10 in which fuel is being burned. The accelerator position sensor measures the position of the accelerator pedal (not shown), in other words, a driver's effort on the accelerator pedal. The oil temperature sensor measures the temperature of lubricating oil in the engine 10. Theses sensors provide outputs to the ECU 25 as representing operating conditions of the engine 10.

The ECU 25 is implemented by a typical microcomputer made up of a CPU, a ROM, a RAM, etc. and performs control programs stored in the ROM to execute the control tasks for the engine 10 as a function of the operating conditions of the engine 10. Specifically, the ECU 25 monitors outputs from the above sensors to calculate a target quantity of fuel to be injected into the engine 10 and the ignition timing of the fuel in the engine 10 and controls operations of the fuel injector 12 and the ignition device 13.

The ECU 25 performs an injection quantity control task in an air-fuel ratio feedback mode using outputs from the A/F sensor 16 and the $O_2$ sensor 17. Specifically, the ECU 25 brings an actual air-fuel ratio of the exhaust gas, as measured by the A/F sensor 16, into agreement with a target air-fuel ratio, as calculated as a function of the operating conditions of the engine 10, in a main feedback mode and also performs a sub-feedback mode using the output of the $O_2$ sensor 17. For example, the ECU 25 brings the target air-fuel ratio into agreement with a stoichiometric air-fuel ratio in the sub-feedback mode.

Figure 2:
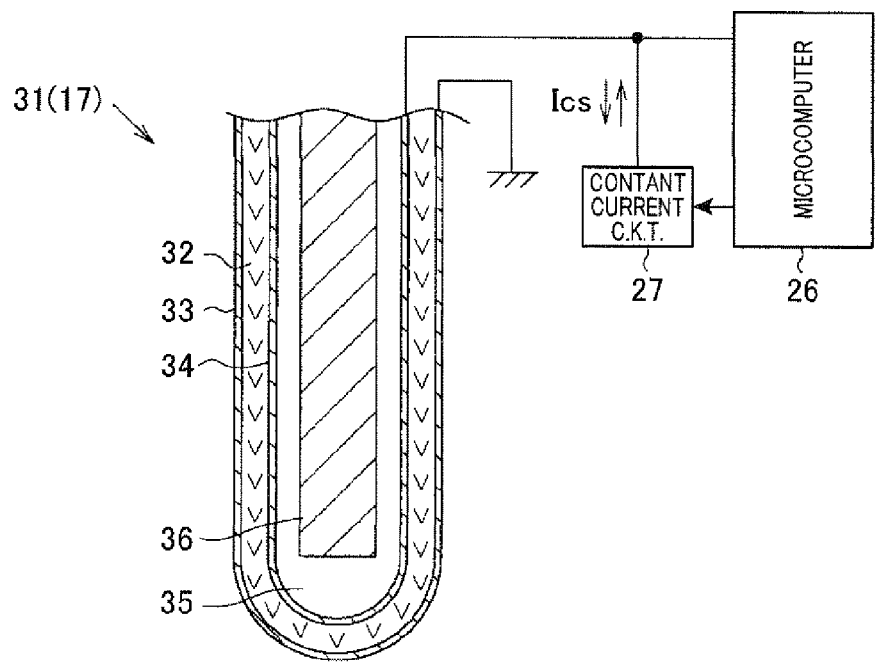
FIG. 2 is a partial longitudinal sectional view which shows a sensing device of an $O_2$ sensor connected electrically to the gas control apparatus installed in the engine control system of FIG. 1.

The $O_2$ sensor 17 is equipped with a cup-shaped sensing device 31, as illustrated in FIG. 2. FIG. 2 is a longitudinal sectional view of the sensing device 31. Although not illustrated, the sensing device 31 is disposed in a hollow housing and sheathed by a cover or a cover assembly. The $O_2$ sensor 17 is, as described above, mounted on the exhaust pipe 14 with the sensing device 31 exposed to the exhaust gas flowing through the exhaust pipe 14.

The sensing device 3, as can be seen from FIG. 2, includes a solid electrolyte body 32 which is of a U-shape in cross section and forms an intermediate layer, an exhaust gas-exposed electrode layer 33, and an air-exposed electrode layer 34. The exhaust gas-exposed electrode layer 33 serves as an exhaust gas-exposed electrode having an outer surface of the sensing device 32. The air-exposed electrode layer 34 serves as an air-exposed electrode having an inner surface of the sensor device 32 which defines an inner air chamber 35. The solid electrolyte body 32 is formed by an oxygen iron-conductive sintered oxide made of $ZrO_2$, $HfO_2$, $ThO_2$, and $Bi_2O_3$ in which CaO, MgO, $Y_2O_3$, and $Yb_2O_3$ are mixed as stabilizers. The exhaust gas-exposed electrode layer 33 and the air-exposed electrode layer 34 are each made of a noble metal such as platinum that is higher in catalytic activity and plated chemically with a porous film. The electrode layers 33 and 34 work as a pair of sensor electrodes. The solid electrolyte body 32 has defines therein the air chamber 35 in which a heater 36 is disposed to produce thermal energy which is great enough to heat the whole of the sensing device 31 to an activatable temperature. The activatable temperature is the temperature at which the $O_2$ sensor 17 is activated to operate properly and, for example, 350° C. to 400° C. The fresh air is supplied to the air chamber 35 so that the concentration of oxygen is kept at a known value in the air chamber 35. In other words, the fresh air is used as a reference gas whose concentration of oxygen is known. The air-exposed electrode layer 34 thus works as a reference gas-exposed electrode.

The solid electrolyte body 32 is exposed at the outer surface thereof to the exhaust gas flowing through the exhaust pipe 14 and at the inner surface thereof to the air in the air chamber 35. The electromotive force is created between the exhaust gas-exposed electrode layer 33 and the air-exposed electrode layer 34 as a function of a difference in concentration of oxygen (i.e., a partial pressure of oxygen) between the exhaust gas and the air. Specifically, the sensing device 31 develops the electromotive force which is difference in potential between when the air-fuel ratio of the exhaust gas is rich and when it is lean. The $O_2$ sensor 17 outputs the electromotive force in the form of an electric signal to inform the ECU 25 that the exhaust gas now flowing through the exhaust pipe 14 is in the rich state or the lean state.

Figure 3:
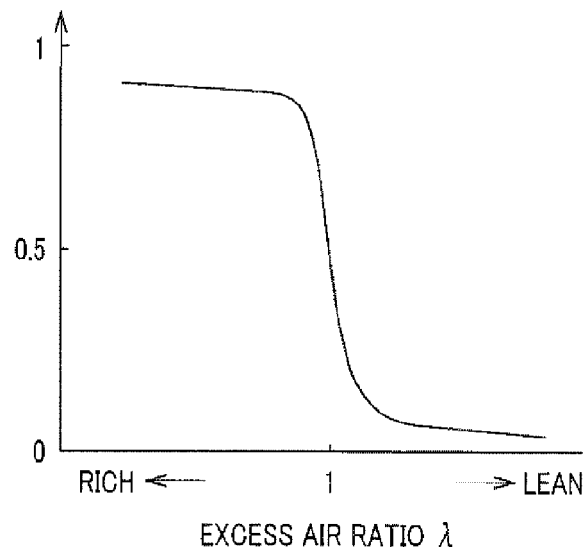
FIG. 3 is an electromotive force characteristic view which demonstrates a relation between a electromotive force, as produced by the sensing device of FIG. 2 and an air-fuel ratio of exhaust gas.

FIG. 3 is an electromotive force characteristic view which demonstrates the electromotive force, as produced by the sensing device 31, and the A/F ratio of the exhaust gas of the engine 10. The horizontal axis represents an excess air ratio λ. λ=1 indicates the stoichiometric air-fuel ratio. A solid curve indicates the electromotive force, as produced by the sensing device 31. The graph shows that the electromotive force changes in level rapidly near the stoichiometric air-fuel ratio. Specifically, in a rich range where the excess air ratio λ is smaller than one (1), the electromotive force will be approximately 0.9V, while in a lean range where the excess air ratio λ is greater than one (1), the electromotive force will be approximately 0V.

Referring back to FIG. 2, the exhaust gas-exposed electrode layer 33 of the sensing device 31 is connected to ground. The air-exposed electrode layer 34 is connected to a microcomputer 26. The electromotive force, as created as a function of the air-fuel ratio (i.e., the concentration of oxygen) in the exhaust gas, is outputted in the form of an electric signal to the microcomputer 26. The microcomputer 26 is installed, for example, in the ECU 25 and serves to calculate the air-fuel ratio based on the output from the sensing device 31. The microcomputer 26 also calculate the speed of the engine 10 and the quantity (i.e., the flow rate) of intake air supplied to the engine 10 using outputs from the sensors, as described above.

When the engine 10 is running, the air-fuel ratio of the exhaust gas sometimes changes successively between the rich and lean states. If the rate or speed at which the $O_2$ sensor 17 is responsive to such a change in air-fuel ratio of the exhaust gas is low, it may result in a drop in performance of the engine 10. For example, it results in an undesirable increase in concentration of oxygen in the exhaust gas when the engine 10 is running in high load conditions.

The responsivity (i.e., the response time or speed) of the $O_2$ sensor 17 when actual air-fuel ratio of the exhaust gas switches between the rich state and the lean state will be described below.

When the air-fuel ratio of exhaust gas emitted from the engine 10 (downstream of the first catalyst 15*a*) changes between the rich and lean sides, it usually involves a change in component composition of the exhaust gas. Some components contained in the exhaust gas immediately before the changing of the air-fuel ratio usually remain residing, which results in a delay in change in level of the output of the $O_2$ sensor 17 in response to the change in the air-fuel ratio of the exhaust gas (i.e., a response time lag of the $O_2$ sensor 17). Specifically, when the air-fuel ratio of the exhaust gas changes, as demonstrated in FIG. 4(*a*), from the rich to lean side, rich components of the exhaust gas such as HC components stay near the exhaust gas-side electrode layer 33, which disturb the reaction of lean components such as NOx components on the sensor electrodes (i.e., the electrode layers 33 and 34). This results in a decrease in responsivity of output of the $O_2$ sensor 17 to the change in the air-fuel ratio to the lean side.

Figure 4A:
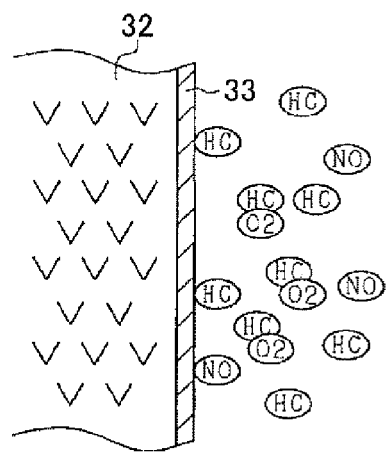
FIG. 4(a) is a partial sectional view of the sensing device of the $O_2$ sensor of FIG. 2 which demonstrates components of exhaust gas staying around the sensing device upon a change in air-fuel ratio from rich to lean.
Figure 4B:
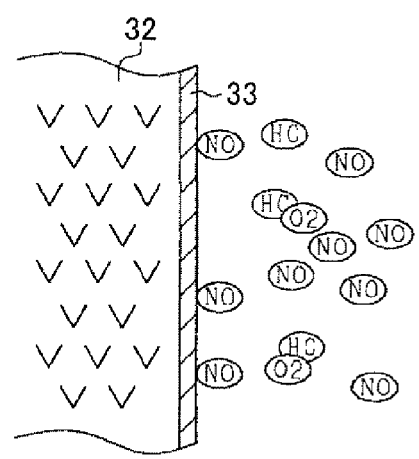
FIG. 4(b) is a partial sectional view of the sensing device of the $O_2$ sensor of FIG. 2 which demonstrates components of exhaust gas staying around the sensing device upon a change in air-fuel ratio from lean to rich.

When the air-fuel ratio of the exhaust gas changes, as illustrated in FIG. 4(*b*), from the lean side to the rich side, the lean components of the exhaust gas such as NOx stay near the exhaust gas-side electrode layer 33, which disturb the reaction of the rich components such as HC on the sensor electrodes (i.e., the electrode layers 33 and 34). This results in a decrease in responsivity of output of the $O_2$ sensor 17 to the change in the air-fuel ratio to the rich side.

Figure 5:
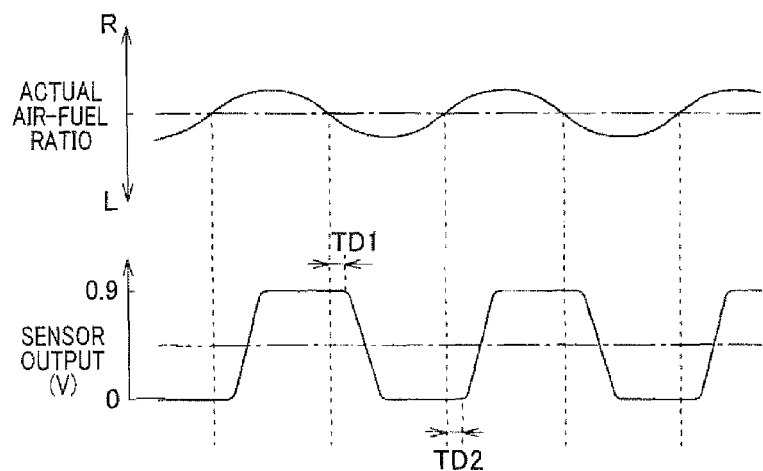
FIG. 5 is a time chart which represents a relation between an actual air-fuel ratio of exhaust gas and an output of the $O_2$ sensor of FIG. 2.

FIG. 5 is a time chart which demonstrates a change in output of the $O_2$ sensor 17.

When the air-fuel ratio of the exhaust gas changes between the rich and lean state, it will cause the output of the $O_2$ sensor 17 to change between 0.9V (i.e., rich) and 0V (i.e., lean). The output of the $O_2$ sensor 17 has a lag in response to a change in air-fuel ratio between the rich and lean side. In the example of FIG. 5, the output of the $O_2$ sensor 17 changes with a lag of TD1 after the air-fuel ratio of the exhaust gas changes from rich to lean, while it changes with a lag of TD2 after the exhaust gas changes from lean to rich.

In order to decrease the above response time lag, the gas control apparatus of this embodiment is designed to evaluate whether the response time of the $O_2$ sensor 17 at least one of when the air-fuel ratio changes to the lean side and when to the rich side has been requested to be changed or not and, if it is affirmative, control the constant current, as will be described later in detail, to regulate the response time of the $O_2$ sensor 17. The regulation of the response time is achieved by passing the electric current through the sensor electrodes (i.e. the electrode layers 33 and 34) in a selected direction.

Specifically, the engine control system also includes, as illustrated in FIG. 2, a constant current circuit 27 that is connected electrically to the air-exposed electrode layer 34 of the $O_2$ sensor 17. The microcomputer 26 controls an operation of the constant current circuit 27 to apply a constant current Ics to the $O_2$ sensor 17. The microcomputer 26 calculates the amount of constant current Ics to be applied to the sensor electrodes and the direction in which the constant current Ics is to flow from the exhaust gas-exposed electrode layer 33 to the air-exposed electrode layer 34 or vice versa.

More specifically, the constant current circuit 27 is designed to apply the constant current Ics to the air-exposed electrode layer 27 in either of opposite directions and also change the constant current Ics. The microcomputer 26 is capable of changing the constant current Ics in a PWM (Pulse-width modulation) mode through the constant current circuit 27. The constant current circuit 27 regulates the constant current Ics based on a duty cycle of a pulse signal outputted from the microcomputer 26 and supplies it to the exhaust gas-exposed electrode layer 33 and the air-exposed electrode layer 34.

In the following discussion, the constant current Ics flowing from the exhaust gas-exposed electrode layer 33 to the air-exposed electrode layer 34 will be referred to as a negative constant current −Ics, while the constant current Ics flowing from the air-exposed electrode layer 34 to the exhaust gas-exposed electrode layer 33 will be referred to as a positive constant current +Ics.

When it is required to increase the response speed, in other words, decrease the response time the $O_2$ sensor 17 takes to react to a change in air-fuel ratio of the exhaust gas from rich to lean (which will also be referred to as a lean sensitivity or a lean response time below), the microcomputer 26 applies the constant current Ics (i.e., the negative constant current −Ics), as illustrated in FIG. 6($a$), so that oxygen molecules ($O_2$) move from the air-exposed electrode layer 34 to the exhaust gas-exposed electrode layer 33 through the solid electrolyte body 32. The supply of oxygen from the air-exposed electrode layer 34 to the exhaust gas-exposed electrode layer 33 accelerates the oxidation reaction of the rich components (HC) staying around the exhaust gas-exposed electrode layer 33, thereby removing the rich components quickly. This facilitates the reaction of the lean components (NOx) on the exhaust gas-exposed electrode layer 33, thus resulting in shortening of the response time of the $O_2$ sensor 17.

Alternatively, when it is required to shorten the response time the $O_2$ sensor 17 takes to react to a change in air-fuel ratio of the exhaust gas from lean to rich (which will also be referred to as a rich sensitivity or a rich response speed below), the microcomputer 26 applies the constant current Ics (i.e., the positive constant current +Ics), as illustrated in FIG. 6($b$), so that oxygen molecules ($O_2$) move from the exhaust gas-exposed electrode layer 33 to the air-exposed electrode layer 34 through the solid electrolyte body 32. The supply of oxygen from the exhaust gas-exposed electrode layer 33 to the air-exposed electrode layer 34 accelerates the reduction reaction of the lean components (NOx) staying around the exhaust gas-exposed electrode layer 33, thereby removing the lean components quickly. This facilitates the reaction of the rich components (HC) on the exhaust gas-exposed electrode layer 33, thus resulting in shortening of the response time of the $O_2$ sensor 17.

Figure 7:
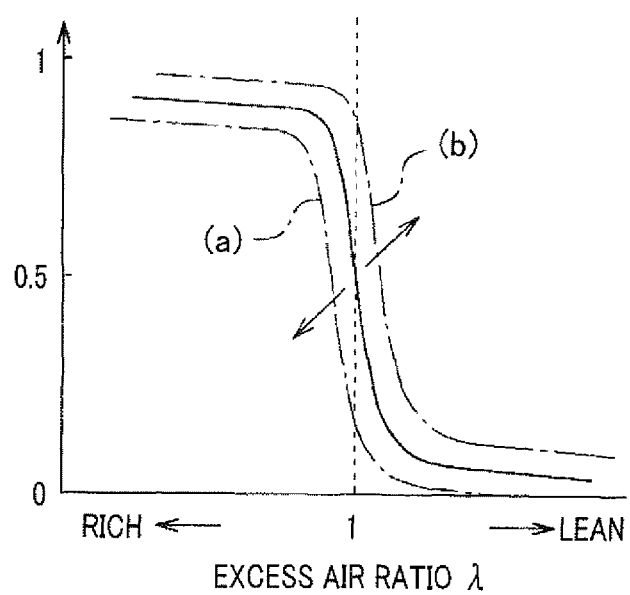
FIG. 7 is an output characteristic view which demonstrates an electromotive force, as produced by the $O_2$ sensor of FIG. 2, for enhancing the rich response time and the lean response time of the $O_2$ sensor.

FIG. 7 is an output characteristic view which demonstrates the electromotive force, as produced by the $O_2$ sensor 17, when the rich response time and the lean response time are enhanced.

The supply of the negative constant current −Ics from the air-exposed electrode layer 34 to the exhaust gas-exposed electrode layer 33 through the solid electrolyte body 32, as already described with reference to FIG. 6($a$), will result in, as indicated by (a) in FIG. 7, a shift of an output characteristic curve to the rich side, in other words, a decrease in electromotive force produced by the $O_2$ sensor 17. Consequently, when an actual air-fuel ratio of the exhaust gas lies within a portion of the rich range near the stoichiometric air-fuel ratio, the output of the $O_2$ sensor 17 indicates the air-fuel ratio to be lean. This means that the response speed of the $O_2$ sensor 17 to a change in air-fuel ratio to the lean side is enhanced.

The supply of the positive constant current +Ics from the exhaust gas-exposed electrode layer 33 to the air-exposed electrode layer 34 through the solid electrolyte body 32, as already described with reference to FIG. 6($b$), will result in, as indicated by (b) in FIG. 7, a shift of the output characteristic curve to the lean side, in other words, an increase in electromotive force produced by the $O_2$ sensor 17. Consequently, when an actual air-fuel ratio of the exhaust gas lies within a portion of the lean range near the stoichiometric air-fuel ratio, the output of the $O_2$ sensor 17 indicates the air-fuel ratio to be rich. This means that the response speed of the $O_2$ sensor 17 to a change in air-fuel ratio to the rich side is enhanced.

FIG. 8 is a flowchart of a response control program to be executed by the microcomputer 26 cyclically at a regular interval to change the response speed of the $O_2$ sensor 17.

In each of steps S11, S12, and S13, it is determined whether a change request is made to change the response speed of the $O_2$ sensor 17 or not. In each of steps S14, S15, S16, and S17, the microcomputer 26 controls the operation of the constant current circuit 27 to regulate the response speed of the $O_2$ sensor 17 according to a result of the determination in step S11, S12, or S13.

Specifically, after entering the program, the routine proceeds to step S11 wherein it is determined whether the engine 10 is running in a cold condition or not. This determination is made by evaluating whether the temperature of coolant for the engine 10 is lower than a given value or not using an output of the coolant temperature sensor 24, whether the temperature of lubricating oil for the engine 10 is lower than a given value or not, or whether the temperature of fuel in a fuel flow path extending to the engine 10 is lower than a given value or not.

If a YES answer is obtained in step S11 meaning that the engine 10 is in the cold condition, and a request is made to increase the response speed of the $O_2$ sensor 17 when the air-fuel ratio of the exhaust gas changes to the rich state, then the routine proceeds to step S14 wherein the microcomputer 26 determines the direction in which the constant current Ics is to flow between the exhaust gas-exposed electrode layer 33 and the air-exposed electrode layer 34 and then applies the positive constant current +Ics to the $O_2$ sensor 17 through the constant current circuit 27. The constant current Ics then flows from the air-exposed electrode layer 34 to the exhaust gas-exposed electrode layer 33, so that oxygen molecules move from the exhaust gas-exposed electrode layer 33 to the air-exposed electrode layer 34. This results in an increase in response speed of the $O_2$ sensor 17 when the engine 10 is in the cold condition. The positive constant current +Ics to be applied to the $O_2$ sensor 17 is preferably determined in advance.

If a NO answer is obtained in step S11, then the routine proceeds to step S12 wherein it is determined whether the engine 10 is running in a high load condition or not. This determination is made based on the operating condition of the engine 10. For example, it is determined whether the quantity of intake air sucked into the cylinder of the engine 10 is greater than a given reference value or not, whether the pressure in the combustion chamber of the engine 10 in which the fuel is burning is greater than a given reference level or not, or whether the position of the accelerator indicates that the engine 10 is required to run in the high load condition or not. If at least one of these conditions is met, the microcomputer 26 concludes that the engine 10 is running in the high load condition. A YES answer is, thus, obtained in step S12 meaning that a request has been made to increase the response speed of the $O_2$ sensor 17 when the air-fuel ratio of the exhaust gas changes to the lean state. The routine proceeds to step S15 wherein the microcomputer 26 applies the negative constant current −Ics to the $O_2$ sensor 17 through the constant current circuit 27. The constant current Ics then flows from the exhaust gas-exposed electrode layer 33 to the air-exposed electrode layer 34, so that oxygen molecules move from the air-exposed electrode layer 34 to the exhaust gas-exposed electrode layer 33. This results in an increase in response speed of the $O_2$ sensor 17 when the engine 10 is in the high load condition. The negative constant current –Ics to be applied to the $O_2$ sensor 17 is preferably determined in advance.

The period of time in which the engine 10 is running in the high load condition usually includes a transient period of time in which the load on the engine 10 is increasing and a high load steady state period of time in which the load on the engine 10 stops increasing, and the engine 10 is kept running in the high load condition. The response speed of the $O_2$ sensor 17 is increased in step S15 both in the transient period of time and the high load steady state period of time, but may be regulated to be different in degree between the transient period of time and the high load steady state period of time. The response speed in the transient period of time is increased more than that in the high load steady state period of time.

Specifically, if a YES answer is obtained in step S12 meaning that the engine 10 is running in the high load condition, the microcomputer 26 may evaluate whether the operation of the engine 10 is in the transient period of time or in the high load steady state period of time. If it is determined that the engine 10 is in the transient period of time, the microcomputer 26 decides that a request is made to decrease the degree to which the response speed of the $O_2$ sensor 17 is increased to be smaller than that in the high load steady state period of time and then regulates a supply of the constant current Isc to the $O_2$ sensor 17. Alternatively, if it is determined that the engine 10 is in the high load steady state period of time, the microcomputer 26 concludes that a request is made to increase the degree to which the response speed of the $O_2$ sensor 17 is increased to be greater than that in the transient period of time and then regulates a supply of the constant current Isc to the $O_2$ sensor 17.

If a NO answer is obtained in step S12, then the routine proceeds to step S13 wherein it is determined whether the fuel has been sprayed into the engine 10 immediately after completion of a fuel cut the engine 10 undergoes or not, and whether a rich fuel injection operation is now being performed to neutralize the catalysts 15a and 15b or not. The rich fuel injection operation is an air-fuel ratio control operation to change the air-fuel ratio to the rich side temporarily based on an output of the $O_2$ sensor 17 in order to eliminate an excess oxygen condition (i.e., an extremely lean state) of the catalysts 15a and 15b upon the completion of the fuel cut to the engine 10. The changing of the fuel ratio to the rich side will cause the atmosphere of the catalysts 15a and 15b to be neutralized, i.e., kept near the stoichiometric air-fuel ratio. At the time when the output of the $O_2$ sensor 17 changes from lean to rich after completion of the fuel cut to the engine 10, the engine control system terminates the rich fuel injection operation. The engine control system decreases the response time of the $O_2$ sensor 17 when the air-fuel ratio changes to the rich side.

If a YES answer is obtained in step S13 meaning that a request is made to decrease the response speed of the $O_2$ sensor 17 when the air-fuel ratio changes to the rich side, then the routine proceeds to step S16 wherein the microcomputer 26 controls the supply of the constant current Ics to decrease the response speed of the $O_2$ sensor 17. Specifically, the microcomputer 26 controls the operation of the constant current circuit 27 to apply the negative constant current –Ics to the $O_2$ sensor 17, as is the case in increasing the response speed of the $O_2$ sensor 17 when the air-fuel ratio changes to the lean side. This causes the oxygen to flow from the air-exposed electrode layer 34 to the exhaust gas-exposed electrode layer 33, thereby decreasing the response speed of the $O_2$ sensor 17 when the rich fuel injection operation is performed to change the air-fuel ratio to the rich side. The degree of the negative constant current –Ics to be applied to the $O_2$ sensor 17 is preferably determined in advance experimentally.

If a NO answer is obtained in all steps S11 to S17, then the routine proceeds to step S17 wherein the microcomputer 26 sets the constant current Ics to zero to keep the response speed of the $O_2$ sensor 17 at the reference value.

The microcomputer 26 does not necessarily need to perform all steps S11 to S13, but may be designed to execute any one or two of them.

FIGS. 9(a) and 9(b) are time charts which represent relations among an actual air-fuel ratio of the exhaust gas, an output of the $O_2$ sensor 17, and the constant current Ics when the lean sensitivity and the rich sensitivity of the $O_2$ sensor 17 are enhanced, respectively.

In FIG. 9(a), changing the air-fuel ratio from rich to lean and from lean to rich cyclically will cause the output of the $O_2$ sensor 17 to switch between 0.9V (i.e., rich) and 0V (i.e., lean) alternately. When it is required to increase the lean sensitivity of the $O_2$ sensor 17 (i.e., the response speed at which the $O_2$ sensor 17 reacts to a change in air-fuel ratio from rich to lean), the negative constant current –Ics is supplied to the $O_2$ sensor 17, so that it flows from the air-exposed electrode layer 34 to the exhaust gas-exposed electrode layer 33 (see FIG. 6(a)). When the air-fuel ratio changes from rich to lean at time t1 or t2, the application of the negative constant current –Ics accelerates the removal of the rich components immediately after time t1 or t2, thereby resulting in an increase in lean sensitivity of the $O_2$ sensor 17. In other words, the time lag TD1, as illustrated in FIG. 5, the output of the $O_2$ sensor 17 experiences when the air-fuel ratio changes to the lean side is decreased.

In addition to the decrease in time lag the output of the $O_2$ sensor 17 experiences when changing from the rich gas level indicating the rich air-fuel ratio to the lean gas level indicating the lean air-fuel ratio, the slope of a line representing the output of the $O_2$ sensor 17 (i.e., the rate at which the output of the $O_2$ sensor 17 changes) is increased as compared with when no current is supplied to the $O_2$ sensor 17. This is because when the output of the $O_2$ sensor 17 changes from rich to lean, the actual air-fuel ratio of the exhaust gas has already changed, as can be seen immediately after time t1 in FIG. 9(a), to lean, but the lean gas usually contains a small quantity of rich components. The flow of the negative constant current –Ics through the $O_2$ sensor 17 in a rich-to-lean transient period of time (i.e., immediately after time t1 in FIG. 9(a)) results in a quick change in output of the $O_2$ sensor 17 from rich to lean, thus leading to an increase in slope of the line representing the output of the $O_2$ sensor 17 in FIG. 9(a).

Figure 6A:
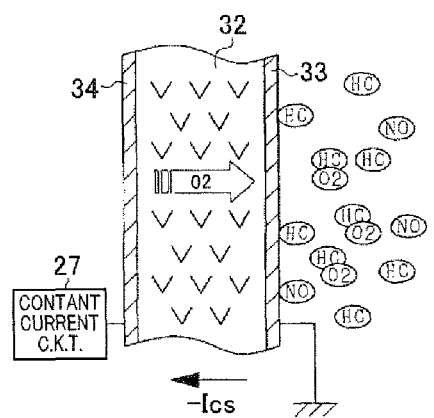
FIG. 6(a) is a partial sectional view of the sensing device of the $O_2$ sensor of FIG. 2 which demonstrates a flow of oxygen when a constant current is applied to the sensing device to enhance the response time of the $O_2$ sensor upon a change in air-fuel ratio from rich to lean.
Figure 6B:
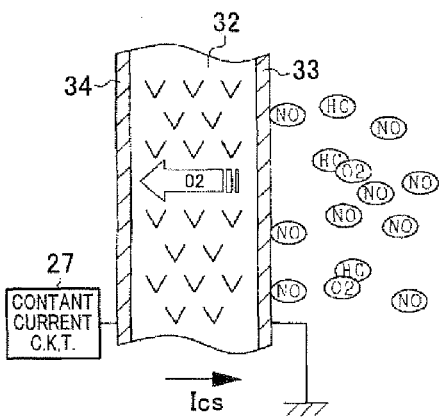
FIG. 6(b) is a partial sectional view of the sensing device of the $O_2$ sensor of FIG. 2 which demonstrates a flow of oxygen when a constant current is applied to the sensing device to enhance the response time of the $O_2$ sensor upon a change in air-fuel ratio from lean to rich.

When it is required to increase the rich sensitivity of the $O_2$ sensor 17 (i.e., the response speed at which the $O_2$ sensor 17 reacts to a change in air-fuel ratio from lean to rich), the positive constant current +Ics is supplied to the $O_2$ sensor 17, so that it flows from the exhaust gas-exposed electrode layer 33 to the air-exposed electrode layer 34 (see FIG. 6(b)). When the air-fuel ratio changes from lean to rich at time t3 or t4 in FIG. 9(b), the application of the positive constant current +Ics accelerates the removal of the lean components immediately after time t3 or t4, thereby resulting in an increase in rich sensitivity of the $O_2$ sensor 17. In other words, the time lag TD2, as illustrated in FIG. 5, the output of the $O_2$ sensor 17 undergoes when the air-fuel ratio changes to the rich side is decreased.

In addition to the decrease in time lag the output of the $O_2$ sensor 17 experiences when changing from the lean gas level to the rich gas level, the slope of the line representing the output of the $O_2$ sensor 17 (i.e., the rate at which the output of the $O_2$ sensor 17 changes) is also increased as compared with when no current is supplied to the $O_2$ sensor 17.

The engine control system of this embodiment offers the following advantages.

The engine control system evaluates whether a request is made to change the rich sensitivity or the lean sensitivity of the $O_2$ sensor 14 or not and, when the request is determined to be made, supplies the constant current to the $O_2$ sensor 17. Specifically, the engine control system is capable of increasing or decreasing the response time of the $O_2$ sensor 17 as needed when the air-fuel ratio changes between the rich and lean state, in other words, accelerating or decelerating the removal of components of the exhaust gas other than that required to be measured in concentration thereof (i.e., the components disturbing the measurement of concentration of oxygen in this embodiment). This is achieved in this embodiment by using the constant current circuit 27 without need for altering the structure of the $O_2$ sensor 17, thus eliminating the need for a complicated structure of the engine control system.

The engine control system is designed to determine which of the lean response speed and the rich response speed of the $O_2$ sensor 17 should be changed depending upon the operating conditions of the engine 10 and thus capable of achieving fine control of the engine 10 according to an instantaneous required change in operating condition of the engine 10.

When it is determined that the engine 10 is required to run in the high load condition, the engine control system determines that a request is made to enhance the lean sensitivity of the $O_2$ sensor 17 and then controls the application of the constant current Ics to the $O_2$ sensor 17, thus enabling the ECU 25 to start to control the air-fuel ratio of mixture to be sprayed into the engine 10 quickly in response to a change in air-fuel ratio of the exhaust gas to the lean side in the high load condition of the engine 10 where the amount of harmful emissions such as NOx is usually increased. This results in a decrease in amount of harmful emissions.

When it is determined that the engine 10 is in the cold condition, the engine control system determines that a request is made to enhance the rich sensitivity of the $O_2$ sensor 17 and then controls the application of the constant current Ics to the $O_2$ sensor 17, thus enabling the ECU 25 to start to control the air-fuel ratio of mixture to be sprayed into the engine 10 quickly in response to a change in air-fuel ratio of the exhaust gas to the rich side in the cold condition of the engine 10 where the amount of harmful emissions such as HC is usually increased. This results in a decrease in amount of harmful emissions.

When the rich fuel injection operation is required to be performed after completion of the fuel cut to the engine 10, the engine control system determines that a request is made to decrease the rich sensitivity of the $O_2$ sensor 17 and then controls the application of the constant current Ics to the $O_2$ sensor 17. This will result in a delay of change in output of the $O_2$ sensor 17 in response to a change in actual air-fuel ratio from lean to rich during the rich fuel injection operation. This causes the rich fuel injection operation to be terminated with a delay after the first catalyst 15a is neutralized. This enables the ECU 25 to neutralize both the first and second catalysts 15a and 15b after completion of the fuel cut to the engine 10, thus controlling the exhaust emissions desirably immediately after the fuel cut.

The engine control system is designed to be capable of varying the level of the constant current Ics to be applied to the $O_2$ sensor 17 in response to the type of a request to change the responsivity of the $O_2$ sensor 17, thus achieving a desired degree of responsivity of the $O_2$ sensor 17 in light of a balance between the lean sensitivity and the rich sensitivity of the $O_2$ sensor 17.

The engine control system determine whether the engine 10, which is required to run in the high load condition, is in the transient period of time or the high load steady state period of time. When the engine 10 is determined to be in the transient period of time, the engine control system increase the responsivity of the $O_2$ sensor 17 more than that in the high load steady state period of time. The quantity of NOx emissions in the transient period of time usually becomes greater than that in the high load steady state period of time. The engine control system, therefore, enhances the responsivity of the $O_2$ sensor 17 in the transient period of time to be greater than that in the high load steady state period of time, thus achieving a desired degree of responsivity of the $O_2$ sensor 17 in light of a balance between the lean sensitivity and the rich sensitivity of the $O_2$ sensor 17.

The engine control system of the second embodiment will be described below which is designed to apply the constant current Ics to the $O_2$ sensor 17 based on values of the air-fuel ratio of the exhaust gas before and after the air-fuel ratio changes between the rich and lean state to change the response speed of the $O_2$ sensor 17. Specifically, when the air-fuel ratio has changed, the microcomputer 26 switches the constant current Ics between the negative constant current −Ics and the positive constant current +Ics. This is effective, especially in the case where the cycle at which the air-fuel ratio changes is relatively long.

Figure 10:
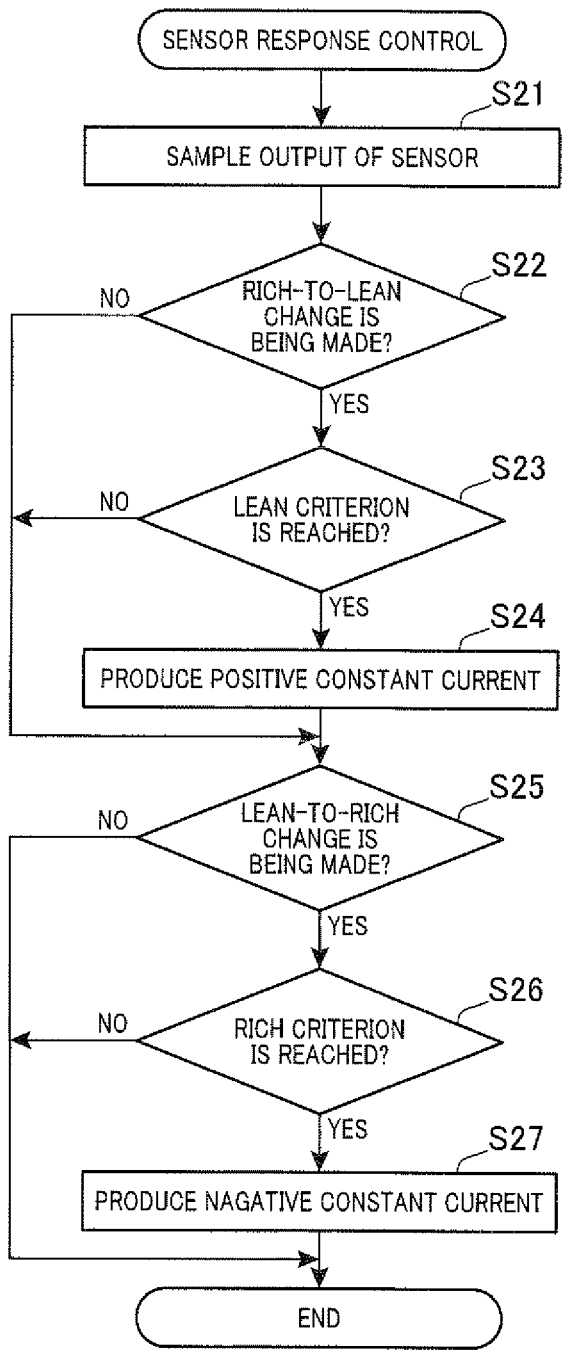
FIG. 10 is a flowchart of a response control program to be executed by a gas sensor control apparatus of the second embodiment of the invention.

FIG. 10 is a flowchart of a response control program to be executed by the microcomputer 26 cyclically at a regular interval to change the response speed of the $O_2$ sensor 17.

After entering the program, the routine proceeds to step S21 wherein the output of the $O_2$ sensor 17 is sampled. The routine proceeds to step S22 wherein it is determined whether the output of the $O_2$ sensor 17 is experiencing a rich-to-lean change or not. This determination is made by comparing an output of the $O_2$ sensor 17, as derived in this sampling cycle, with that, as derived one sampling cycle earlier. If a YES answer is obtained, then the routine proceeds to step S23 wherein the output of the $O_2$ sensor 17 has reached a given lean criterion THL or not. The lean criterion THL is a value for use in determining whether the output of the $O_2$ sensor 17 has reached a lean gas level (i.e., 0V) representing the lean air-fuel ratio or not. The lean criterion THL is set to, for example, 0.1V.

If a YES answer is obtained in step S23, then the routine proceeds to step S24 wherein the positive constant current +Ics is produced. Specifically, the microcomputer 26 controls the operation of the constant current circuit 27 to apply the positive constant current +Ics to the $O_2$ sensor 17 so that oxygen moves from the exhaust gas-exposed electrode layer 33 to the air-exposed electrode layer 34.

The routine proceeds to step S25 wherein it is determined whether it is determined whether the output of the $O_2$ sensor 17 is experiencing a lean-to-rich change or not. This determination is made by comparing an output of the $O_2$ sensor 17, as derived in this sampling cycle, with that, as derived in one sampling cycle earlier. If a YES answer is obtained, then the routine proceeds to step S26 wherein the output of the $O_2$ sensor 17 has reached a given rich criterion THR or not. The rich criterion THR is a value for use in determining whether the output of the $O_2$ sensor 17 has reached a rich gas level (i.e., 0.9V) representing the rich air-fuel ratio or not. The rich criterion THR is set to, for example, 0.8V.

If a YES answer is obtained in step S26, then the routine proceeds to step S274 wherein the negative constant current=Ics is produced. Specifically, the microcomputer 26 controls the operation of the constant current circuit 27 to apply the negative constant current −Ics to the $O_2$ sensor 17 so that oxygen moves from the air-exposed electrode layer 34 to the exhaust gas-exposed electrode layer 33.

Figure 11:
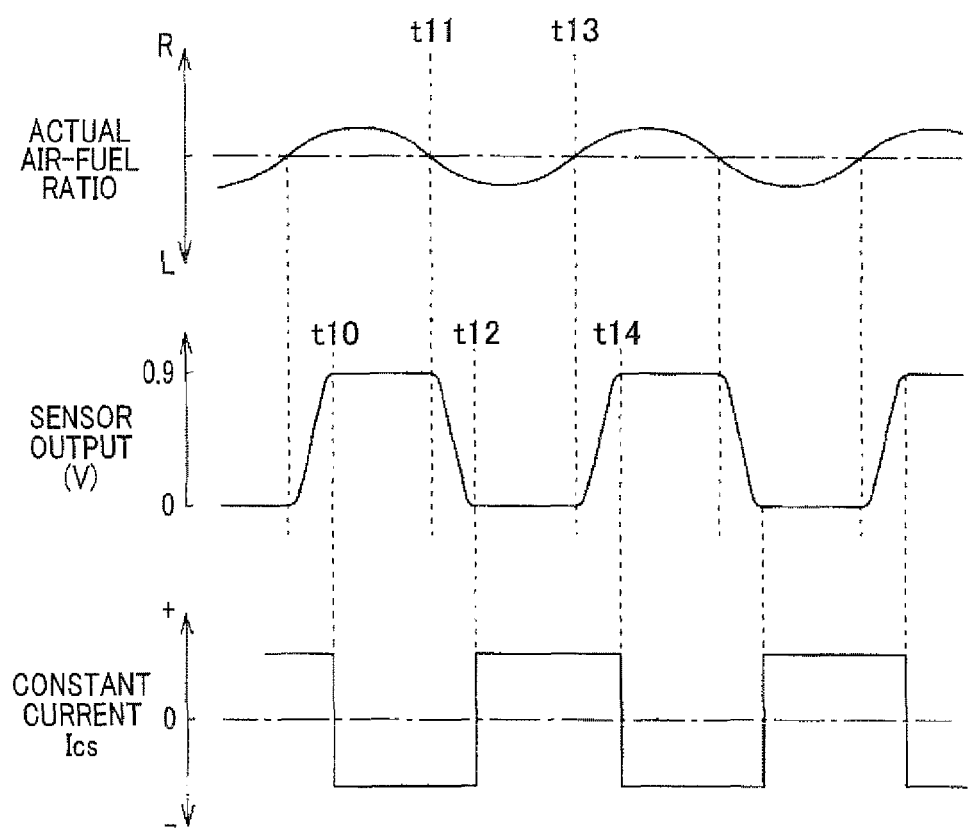
FIG. 11 is a time chart which demonstrates a relation among an actual air-fuel ratio of exhaust gas, an output of an $O_2$ sensor, and constant current applied to the $O_2$ sensor in the response control program of FIG. 10.

FIG. 11 is a time chart which represents a relation among an actual air-fuel ratio of the exhaust gas, an output of the $O_2$ sensor 17, and the constant current Ics when the lean sensitivity and the rich sensitivity of the $O_2$ sensor 17 are enhanced, respectively.

The changing the air-fuel ratio from rich to lean and from lean to rich cyclically will cause the output of the $O_2$ sensor 17 to switch between 0.9V (i.e., rich) and 0V (i.e., lean) alternately. In a period of time (i.e., time t10 to time t12) between when the output of the $O_2$ sensor 17 converges on the rich gas level (0.9V) and when that converges on the lean gas level (0V), the negative constant current −Ics is applied to the $O_2$ sensor 17. In a period of time (i.e., time t12 to time t13) between when the output of the $O_2$ sensor 17 converges on the lean gas level (0V) and when that converges on the rich gas level (0.9V), the positive constant current +Ics is applied to the $O_2$ sensor 17.

At time t11 when the air-fuel ratio of the exhaust gas changes from rich to lean, the negative constant current −Ics is flowing through the exhaust gas-electrode layer 33 and the air-exposed electrode layer 34, so that oxygen travels from the air-exposed electrode layer 34 to the exhaust gas-exposed electrode layer 33 (see FIG. 6(a)). This causes the removal of the rich components to be accelerated immediately after the air-fuel ratio changes to the lean side, thereby resulting in an increase in rich response speed of the $O_2$ sensor 17. Subsequently, at time t12 when the output of the $O_2$ sensor 17 reaches the lean criterion THL, the constant current Ics to be applied to the $O_2$ sensor 17 is changed from the negative constant current −Ics to the positive constant current +Ics.

At time t13 when the air-fuel ratio of the exhaust gas changes from lean to rich, the positive constant current +Ics is flowing through the exhaust gas-electrode layer 33 and the air-exposed electrode layer 34, so that oxygen travels from the exhaust gas-exposed electrode layer 33 to the air-exposed electrode layer 34 (see FIG. 6(b)). This causes the removal of the rich components to be accelerated immediately after the air-fuel ratio changes to the rich side, thereby resulting in an increase in lean response speed of the $O_2$ sensor 17. Subsequently, at time t14 when the output of the $O_2$ sensor 17 reaches the rich criterion THR, the constant current Ics to be applied to the $O_2$ sensor 17 is changed from the positive constant current +Ics to the negative constant current −Ics.

In the example of FIG. 11, when the air-fuel ratio changes from rich to lean, and time t12 when a change in output (i.e., the electromotive force) of the $O_2$ sensor 17 to the lean side converges on zero is reached, the microcomputer 26 starts to supply the positive constant current +Ics to the $O_2$ sensor 17 to accelerate the removal of the lean components of the exhaust gas. When the air-fuel ratio changes from lean to rich, and time t14 when a change in output (i.e., the electromotive force) of the $O_2$ sensor 17 to the rich side converges on zero is reached, the microcomputer 26 starts to supply the negative constant current −Ics to the $O_2$ sensor 17 to accelerate the removal of the rich components of the exhaust gas.

Consequently, in addition to the decrease in time lag the output of the $O_2$ sensor 17 experiences when changing from the rich gas level to the lean gas level, the slope of the line representing the output of the $O_2$ sensor 17 (i.e., the rate at which the output of the $O_2$ sensor 17 changes) is increased as compared with when no current is supplied to the $O_2$ sensor 17. This is because when the output of the $O_2$ sensor 17 changes from the rich gas level to the lean gas level, the actual air-fuel ratio of the exhaust gas has already changed, as can be seen from time t11 to time t12 in FIG. 11, but the lean gas usually contains a small quantity of rich components. The flow of the negative constant current −Ics through the $O_2$ sensor 17 in a rich-to-lean period of time (i.e., between time t11 and time t12 in FIG. 11) results in a quick change in output of the $O_2$ sensor 17 from the rich gas level to the lean gas level, thus leading to an increase in slope of the line representing the output of the $O_2$ sensor 17.

Similarly, when the actual air-fuel ratio changes from lean to rich, the slope of the line representing the output of the $O_2$ sensor 17 (i.e., the rate at which the output of the $O_2$ sensor 17 changes) is also increased as compared with when no current is supplied to the $O_2$ sensor 17 in addition to the decrease in time lag the output of the $O_2$ sensor 17 experiences when changing from the lean gas level to the rich gas level.

Figure 12A:
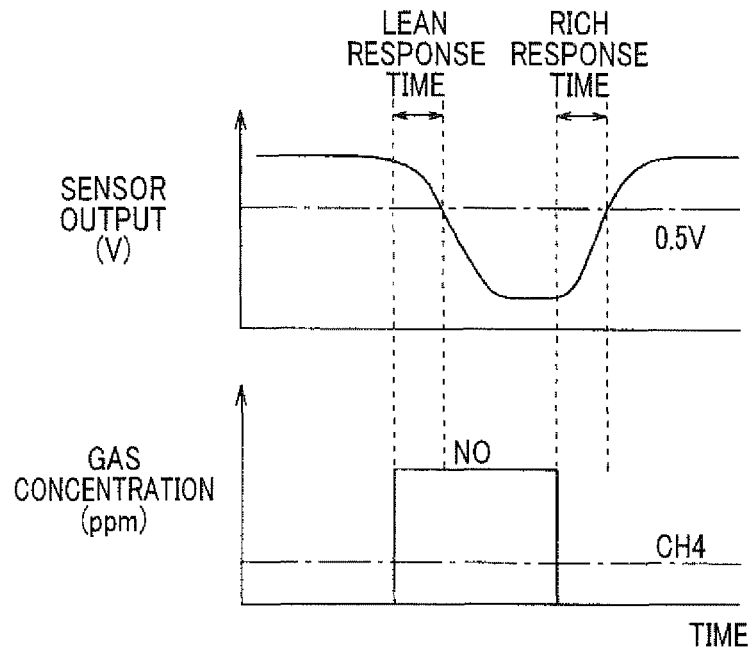
FIG. 12(a) is a view which represents environmental conditions in which tests were performed to evaluate a change in response time of an $O_2$ sensor.
Figure 12B:
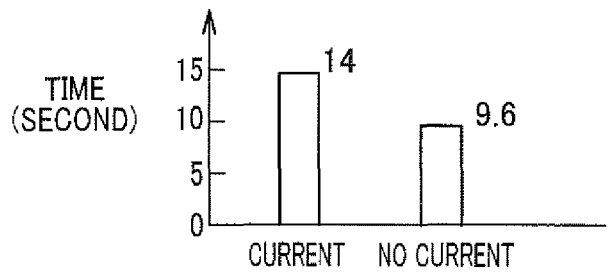
FIG. 12(b) is a graph which shows results of the tests performed in FIG. 12(a) when the response time of an $O_2$ sensor upon a change in air-fuel ration from rich to lean is enhanced.
Figure 12C:
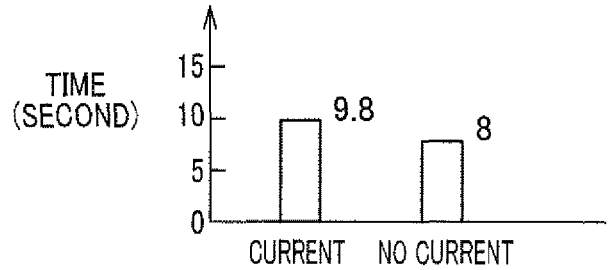
FIG. 12(c) is a graph which shows results of the tests performed in FIG. 12(a) when the response time of an $O_2$ sensor upon a change in air-fuel ration from lean to rich is enhanced.

The inventors of this application performs tests to evaluate the response time of the $O_2$ sensor 17. FIG. 12(a) shows environmental conditions in which the tests were performed. FIGS. 12(b) and 12(c) show results of the tests.

We simulated actual environmental conditions of the automotive vehicle. Specifically, as illustrated in FIG. 12(a), the lean gas (NO) was injected temporarily into the exhaust pipe while the rich gas ($CH_4$) was being injected into the exhaust pipe. The lean gas response time and the rich gas response time the $O_2$ sensor 17 takes to react to a change in air-fuel ratio to lean and rich were measured by defining 0.5V as a reference level at which the output of the $O_2$ sensor 17 is determined to have changed between the rich and lean state.

FIGS. 12(b) and 12(c) represent the lean gas response time and the rich gas response time, respectively. We measured times required by the $O_2$ sensor 17 to produce an output in response to a change in air-fuel ratio from rich to lean when the negative constant current −Ics was being supplied to the $O_2$ sensor 17 and when not to, respectively. Similarly, we also measured times required by the $O_2$ sensor 17 to produce an output in response to a change in air-fuel ratio from lean to rich when the positive constant current +Ics was being supplied to the $O_2$ sensor 17 and when not to, respectively. The graphs of FIGS. 12(b) and 12(c) show that the lean gas response time and the rich gas response time of the $O_2$ sensor 17 are both decreased by application of the constant current Ics to the $O_2$ sensor 17.

The engine control system may be designed to change the constant current Ics to be applied to the $O_2$ sensor 17 based on the operating conditions of the engine 10 such as the quantity of intake air sucked into the engine 10 and/or the speed of the engine 10.

Figure 13A:
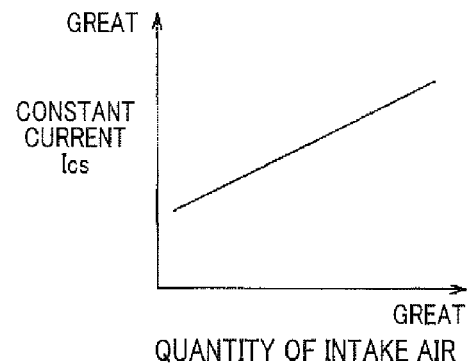
FIG. 13(a) is a graph which illustrates a relation of constant current to be applied to an $O_2$ sensor to the quantity of intake air supplied to an internal combustion engine.
Figure 13B:
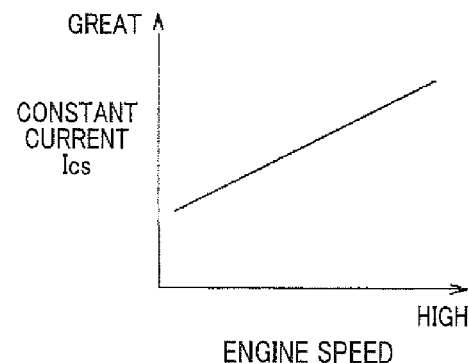
FIG. 13(b) is a graph which illustrates a relation of constant current to be applied to an $O_2$ sensor to the speed of an internal combustion engine.

For example, the greater the quantity of intake air to the engine 10, the greater the degree to which the intake air disturbs the reaction of the $O_2$ sensor 17 to a change in air-fuel ratio of the exhaust gas. The engine control system may, therefore, increase the constant current Ics with an increase in quantity of intake air, as illustrated in FIG. 13(a). Additionally, the greater the speed of the engine 10, the greater the degree to which the intake air disturbs the reaction of the $O_2$ sensor 17 to a change in air-fuel ratio of the exhaust gas. The engine control system may, therefore, increase the constant current Ics with an increase in quantity of intake air, as illustrated in FIG. 13(b). Instead of the quantity of intake air, the quantity of exhaust gas, as measured actually or calculated, may be employed.

The engine control system of the second embodiment offers the following advantages.

The engine control system is, as described above, designed to apply the constant current Ics to the exhaust gas-exposed electrode layer 33 and the air-exposed electrode layer 34 of the $O_2$ sensor 17 in a selected direction based on values of the air-fuel ratio of the exhaust gas, as sampled before and after the air-fuel ratio changes between the rich and lean state, thereby advancing the time when the rich state or the lean state to which the air-fuel ratio of the exhaust gas changes is to be detected. This is accomplished by using the constant current circuit 27 without need for altering the structure of the $O_2$ sensor 17, thus eliminating the need for a complicated structure of the engine control system.

At the time when the output of the $O_2$ sensor 17 converges on the lean gas level or the rich gas level, the microcomputer 26 reverses the direction in which the constant current Ics is to be supplied to flow between the exhaust gas-exposed electrode layer 33 and the air-exposed electrode layer 34. This is achieved easily by controlling the operation of the constant current circuit 27.

The microcomputer 26 is designed to control the constant current Ics as a function of the operating conditions of the engine 10, thus ensuring the response time of the $O_2$ sensor 17 which matches the operating conditions of the engine 10.

Other Modifications

The engine control system of each of the above embodiments may be modified as follows.

The engine control system of the first embodiment may be designed to evaluate the state of aging of the $O_2$ sensor 17 and determines whether a request to change the response time of the $O_2$ sensor 17 is made or not based on the evaluated state of aging. For example, the evaluation of the state of aging is achieved based on the rate at which the level of output of the $O_2$ sensor 17 drops upon a cut of fuel to the engine 10. The microcomputer 26 determines that the degree of aging of the $O_2$ sensor 17 is greater as the rate of the drop in level of the output of the $O_2$ sensor 17 is smaller. When the rate of the drop in level of the output of the $O_2$ sensor 17 is smaller than a given reference level, the microcomputer 26 determines that the request is made to change the response time of the $O_2$ sensor 17 and applies the constant current Ics to the $O_2$ sensor 17. A determination of which of the lean response time and the rich response time should be increased is preferably made based on the operating conditions of the engine 10. The constant current Ics may also be regulated as a function of the degree of aging of the $O_2$ sensor 17. For example, the constant current Ics is increased with an increase in degree of the aging.

The engine control system of the second embodiment may be designed to increase the constant current Ics when the actual air-fuel ratio of the exhaust gas changes from lean to rich upon completion of the fuel cut to the engine 10 as compared with when the actual air-fuel ratio of the exhaust gas changes from lean to rich when the fuel is not cut to the engine. For instance, when the supply of fuel to the engine 10 has been cut upon deceleration of the vehicle, it will cause the exhaust pipe 14 to be still filled with the air at the time when the vehicle starts to accelerate subsequently. A great deal of oxygen, thus, stays around the $O_2$ sensor 17 immediately after the completion of the fuel cut to the engine 10 (i.e., upon the start of acceleration of the vehicle). In order to eliminate such a condition quickly, the microcomputer 26 increases the positive constant current +Ics to increase the amount of oxygen to be moved from the exhaust gas-exposed electrode layer 33 to the air-exposed electrode layer 34 as compared with when the fuel is not cut to the engine 10. This results in an increase in response speed of the $O_2$ sensor 17 upon completion of the fuel cut to the engine 10.

The engine control system of the second embodiment may be designed to increase the constant current Ics when the actual air-fuel ratio of the exhaust gas changes from rich to lean upon completion of increasing the load on the engine during acceleration of the engine 10 in order to protect parts of an exhaust system for the engine 10 as compared with when the actual air-fuel ratio of the exhaust gas changes from rich to lean when the load on the engine 10 is not increased. When the load on the engine 10 is increased during the acceleration of the engine 10, it will cause the exhaust pipe 14 to be still filled with the rich components. A great deal of the rich components, thus, stays around the $O_2$ sensor 17 immediately after the completion of increasing the load on the engine 10. In order to eliminate such a condition quickly, the microcomputer 26 increases the negative constant current −Ics to increase the amount of oxygen to be moved from the air-exposed electrode layer 34 to the exhaust gas-exposed electrode layer 33 as compared with when the load on the engine 10 is not increased. This results in an increase in response speed of the $O_2$ sensor 17 upon completion of increasing the load on the engine 10.

Figure 14:
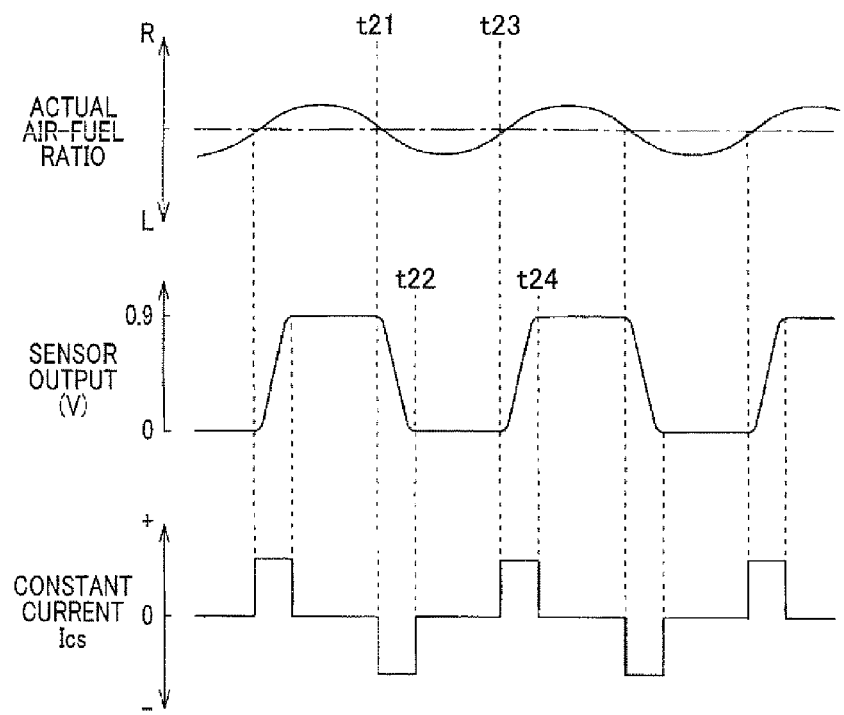
FIG. 14 is a time chart which demonstrates a relation among an actual air-fuel ratio of exhaust gas, an output of an $O_2$ sensor, and constant current applied to the $O_2$ sensor in a modification of the second embodiment.

The microcomputer 26 of the second embodiment may supply the constant current Ics upon a change in air-fuel ratio of the exhaust gas from rich to lean in the manner different from that in FIG. 11. For example, the microcomputer 26 may, as illustrated in FIG. 14, supply the constant current Ics only in a transient period of time for which the actual air-fuel ratio of the exhaust gas is changing between the rich and lean state. In the example of FIG. 14, the negative constant current −Ics is supplied to the $O_2$ sensor 17 only in a period of time between time t21 and time t22 for which the output of the $O_2$ sensor 17 is changing from the rich gas level (0.9V) to the lean side, while the positive constant current +Ics is supplied to the $O_2$ sensor 17 only in a period of time between time t23 and time t24 for which the output of the $O_2$ sensor 17 is changing from the lean gas level (0V) to the rich side. No constant current is supplied for another period of time.

Figure 15A:
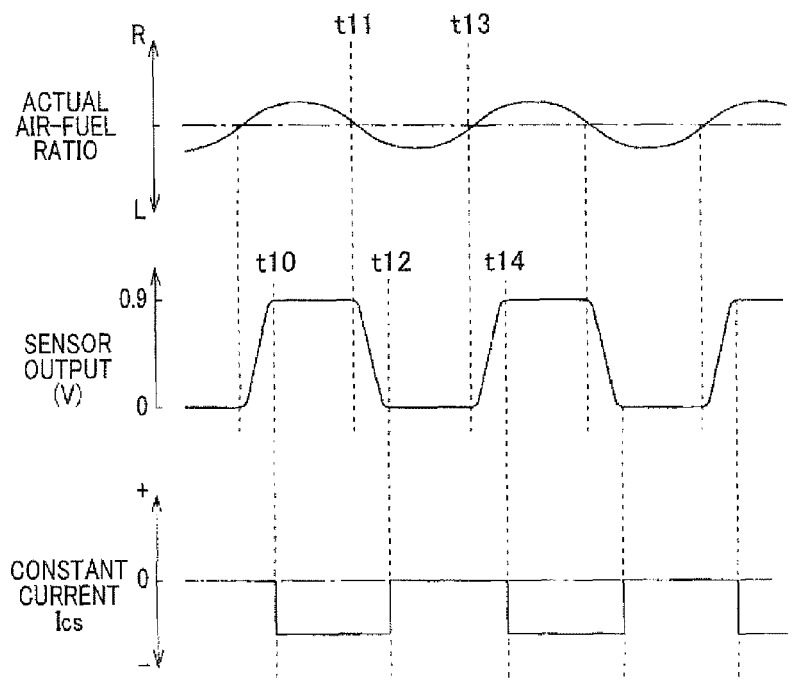
FIG. 15(a) is a time chart which demonstrates a relation among an actual air-fuel ratio of exhaust gas, an output of an $O_2$ sensor, and constant current applied to the $O_2$ sensor in another modification of the second embodiment.
Figure 15B:
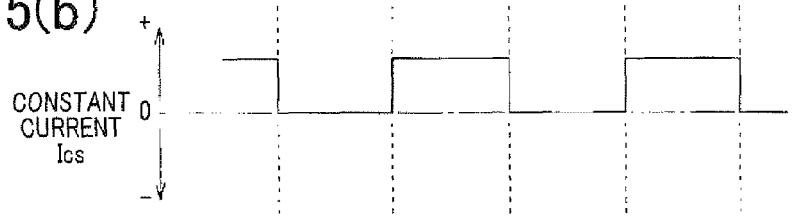
FIG. 15(b) is a time chart which demonstrates time at which a constant current to be applied to the $O_2$ sensor in another modification of the second embodiment.
Figure 15C:
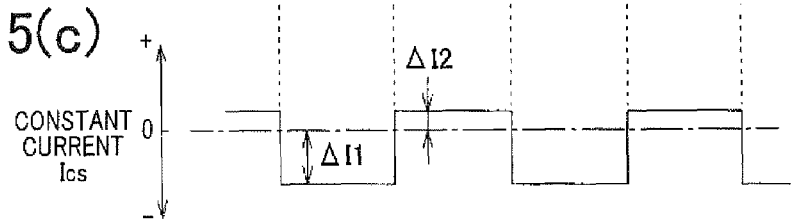
FIG. 15(c) is a time chart which demonstrates time at which a constant current to be applied to the $O_2$ sensor in another modification of the second embodiment.

The microcomputer 26 of the second embodiment may alternatively be designed to supply the constant current Ics in any of manners, as demonstrated in FIGS. 15(a), 15(b), and 15(c). The changes in an actual air-fuel ratio of the exhaust gas and the output of the $O_2$ sensor 17 are the same as those in FIG. 11, and explanation thereof in detail will be omitted here.

When it is required to change the response time of the $O_2$ sensor 17, the microcomputer 26 supplies the constant current Ics1, as illustrated in FIG. 15(a), to the $O_2$ sensor 17. Specifically, the microcomputer 26 supplies the negative constant current −Ics1 to the $O_2$ sensor 17 for a period of time (i.e., between time T10 and time t12) from when the output of the $O_2$ sensor 17 converges on the rich gas level (0.9V) to when the output of the $O_2$ sensor 17 changes to the lean side and reaches the lean gas level (0V) and supplies no constant current for another period of time.

The microcomputer 26 may alternatively be designed, as illustrated in FIG. 15(b), to supply the positive constant current +Ics2 to the $O_2$ sensor 17 for a period of time (i.e., between time t12 and time t13) from when the output of the $O_2$ sensor 17 converges on the lean gas level (0V) to when the output of the $O_2$ sensor 17 changes to the rich side and reaches the rich gas level (0.9V) and supplies no constant current for another period of time. This enhances the response time of the $O_2$ sensor 17 only when the air-fuel ratio changes from rich to lean.

The microcomputer 26 may alternatively be designed, as illustrated in FIG. 15(c), to switch between the positive constant current +Ics3 and the negative constant current −Ics3 upon a change in air-fuel ratio between the rich and lean side. The amount ΔI2 of the positive constant current +Ics3 is, however, smaller than the amount ΔI1 of the negative constant current −Ics3. In other words, the amount of oxygen which is to be supplied by the negative constant current −Ics3 from the air-exposed electrode layer 34 to the exhaust gas-exposed electrode layer 33 is different from that which is to be supplied by the positive constant current +Ics3 from the exhaust gas-exposed electrode layer 33 to the air-exposed electrode layer 34. The former amount is set to be greater than the latter amount.

Specifically, the amount ΔI1 of the negative constant current −Ics3 to be applied to the $O_2$ sensor 17 from when the output of the $O_2$ sensor 17 converges on the rich gas level to when it converges on the lean gas level is set greater than the amount ΔI2 of the positive constant current +Ics3 to be applied to the $O_2$ sensor 17 from when the output of the $O_2$ sensor 17 converges on the lean gas level to when it converges on the rich gas level. This causes the amount of oxygen which is to be supplied by the positive constant current +Ics3 from the exhaust gas-exposed electrode layer 33 to the air-exposed electrode layer 34 to be smaller than that which is to be supplied by the negative constant current −Ics3 from the air-exposed electrode layer 34 to the exhaust gas-exposed electrode layer 33. This decreases an excessive amount of oxygen drawn from the exhaust gas-exposed electrode layer 33 when the air-fuel ratio is in the lean state. The amount ΔI1 of the negative constant current −Ics3 may alternatively be set to smaller than the amount ΔI2 of the positive constant current +Ics3 as needed.

The constant current circuit 27 may alternatively be connected to the exhaust gas-exposed electrode layer 33 of the $O_2$ sensor 17. Constant current circuits may be joined to both the exhaust gas-exposed electrode layer 33 and the air-exposed electrode layer 34, respectively.

Figure 16:
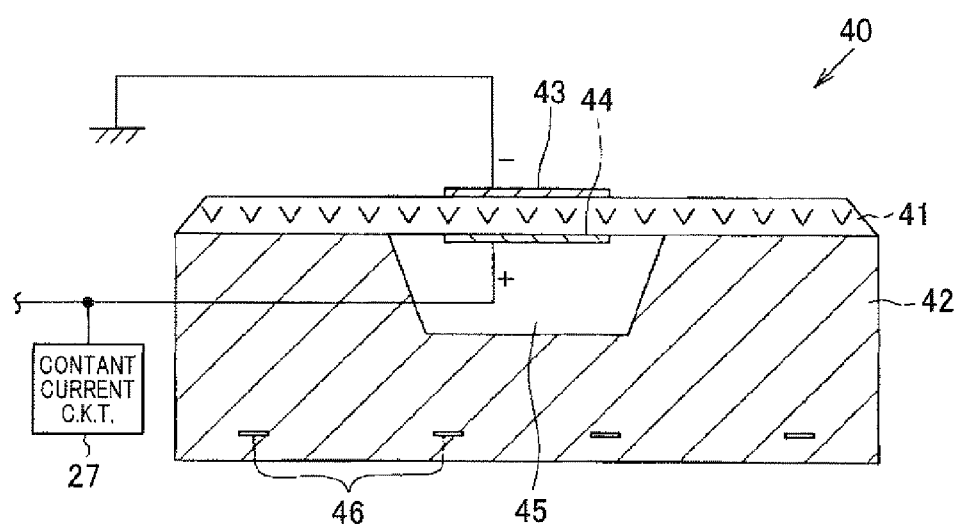
FIG. 16 is a transverse sectional view which illustrates a modification of an $O_2$ sensor for use with a gas sensor control apparatus.

The $O_2$ sensor 17 is, as described above, of a thimble type, but a planar type of $O_2$ sensor may alternatively be employed. FIG. 16 is a transverse sectional view which illustrates the planar type of $O_2$ sensing device 40. The sensing device 40 has a length extending perpendicular to the drawing and is installed in a hollow housing and sheathed by a cover or a cover assembly.

The sensing device 40 includes a stack of a solid electrolyte layer 41 formed by a rectangular partially-stabilized zirconia sheet and an insulating layer 42 made of a high thermal conductive ceramic. An protective layer (not shown) surrounds the sensing device 40. The sensing device 40 also includes an outer electrode 43 and an inner electrode 44 affixed to opposed surfaces of the solid electrolyte layer 41. The insulating layer 42 has defined therein an air duct 45 to which the inner electrode 44 is exposed. The insulating layer 43 also has a heater 46 embedded therein. The heater 46 is made of a heating strip or wire and supplied with electric power from, for example, a storage batter installed in the vehicle to heat the whole of the sensing device 40 up to a desired temperature.

The sensing device 40 is exposed at an outer surface thereof to the exhaust gas flowing through the exhaust pipe 14. The fresh air is introduced into the air duct 45. The outer electrode 43 is, therefore, exposed to the exhaust gas, while the inner electrode 44 is exposed to the air. The electromotive force is created between the outer electrode 43 and the inner electrode 44 as a function of a difference in concentration of oxygen (i.e., a partial pressure of oxygen) between the exhaust gas and the air. Specifically, the sensing device 40 develops the electromotive force which is difference in potential between when the air-fuel ratio of the exhaust gas is rich and when it is lean.

The constant current circuit 27 is connected electrically to the inner electrode 44. The microcomputer 26 supplies, like in the above embodiments, the constant current Ics to the sensing device 40. How to control the constant current Ics is the same as in the above embodiments, and explanation thereof in detail will be omitted here.

The engine control system of the above embodiments may alternatively be designed to regulate the response time of the A/F sensor 16. Specifically, the microcomputer 26 determines whether a request is made to change the response time of the A/F sensor 16 and control the supply of the constant current Ics to the A/F sensor 16 according to the type of the request.

The engine control system of the above embodiments may also be used with a typical HC sensor made up of a solid electrolyte body and a pair of electrodes affixed to opposed surfaces of the solid electrolyte body. The microcomputer 26 determines whether a request is made to change the response time the HC sensor takes to react to a change in concentration of HC in the exhaust gas and control the supply of the constant current Ics which is to flow through the electrodes on the solid electrolyte body according to the type of the request. When it is required to shorten the response time of the HC sensor, the microcomputer 26 supplies the positive current +Isc to the HC sensor so that oxygen moves from one of the electrodes which is exposed to the exhaust gas to the other.

The engine control system of the above embodiments may also be used with a typical NOx sensor made up of a solid electrolyte body and a pair of electrodes affixed to opposed surfaces of the solid electrolyte body. The microcomputer 26 determines whether a request is made to change the response time the NOx sensor takes to react to a change in concentration of NOx in the exhaust gas and control the supply of the constant current Ics which is to flow through the electrodes on the solid electrolyte body according to the type of the request. When it is required to shorten the response time of the NOx sensor, the microcomputer 26 supplies the negative current −Isc to the HC sensor so that oxygen moves from one of the electrodes which is exposed to the air to the other.

The microcomputer 26 of the engine control system, as described above, works to improve the response speed or time of the $O_2$ sensor 17 which measures the concentration of oxygen contained in the exhaust gas emitted from the engine 10, but may be engineered to change the response time of a gas sensor which produces an output in response to a change in component of gas. For instance, the microcomputer 26 is designed to change the response time of the A/F sensor 16 in FIG. 1.

The microcomputer 26 may control the supply of the constant current Ics to the HC sensor in response to a change in concentration of HC (Hydrocarbon) components between when the HC components exit in the exhaust gas and when no HC components or a minute amount of the HC components exists in the exhaust gas. For example, the microcomputer 26 changes how to supply the constant current Ics to the HC sensor based on the component of the exhaust gas (e.g., the concentration of the HC components) before the change in the concentration of the HC components. Similarly, the microcomputer 26 may control the supply of the constant current Ics to the NOx sensor in response to a change in concentration of NOx (Nitrogen Oxides) components between when the NOx components exit in the exhaust gas and when no NOx components or a minute amount of the NOx components exists in the exhaust gas. For example, the microcomputer 26 changes how to supply the constant current Ics to the NOx sensor based on the component of the exhaust gas (e.g., the concentration of the NOx components) before the change in the concentration of the NOx components. The microcomputer 26 may alternatively be designed for exhaust emissions from calcinators or combustion furnaces.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas sensor control apparatus which is used with an internal combustion engine control system which is equipped with a gas sensor to detect an air-fuel ratio for exhaust gas from an internal combustion engine as gas to be measured and controls the air-fuel ratio to a given target value based on a result of detection of the air-fuel ratio by the gas sensor, said gas sensor being equipped with a solid electrolyte body, an exhaust gas side electrode and a reference chamber side electrode which are disposed as a pair of sensor electrodes on a surface of the solid electrolyte body, the exhaust gas side electrode being exposed to the exhaust gas, the reference chamber side electrode being exposed to a reference gas in a reference chamber, the gas sensor control apparatus comprising:

a constant current supply connected electrically to at least one of said pair of sensor electrodes and configured to supply a constant current to the at least one of said pair of sensor electrodes;

a decision unit configured to decide whether a change request for either of an output characteristic of said gas sensor at a lean change time when the air-fuel ratio changes from rich to lean and an output characteristic of said gas sensor at a rich change time when the air-fuel ratio changes from lean to rich has been made or not to decide whether a change request for changing the output characteristic of the gas sensor including a detection response to a change in the air-fuel ratio has been made or not;

a current controller configured to control the constant current supply so that the constant current flows in a direction in which oxygen is supplied from the reference chamber side electrode to the exhaust gas side electrode through said solid electrolyte body when it is decided by the decision unit that the change request has been made for enhancing the detection response at the lean change time as the output characteristic at the lean change time and also configured to control the constant current supply so that the constant current flows in a direction in which oxygen is supplied from the exhaust gas side electrode to the reference chamber side electrode through said solid electrolyte body when it is decided by the decision unit that the change request has been made for enhancing the detection response at the rich change time as the output characteristic at the rich change time; and an operating condition detector configured to detect an operating condition of the internal combustion engine, wherein said decision unit is configured to decide that the change request has been made to enhance the detection response at the lean change time when it is decided based on the engine operating condition, as detected by said operating condition detector, that the internal combustion engine is in a high-load operating condition, and wherein said current controller is configured to control said constant current supply based on the change request to enhance the detection response at the lean change time.

2. A gas sensor control apparatus as set forth in claim 1, wherein when it is decided based on the engine operating condition, as detected by said operating condition detector, that the internal combustion engine is in a cold condition, said decision unit is configured to decide that the change request has been made to enhance the detection response at the rich change time, and wherein said current controller is configured to control said constant current supply based on the change request to enhance the detection response at the rich change time.

3. A gas sensor control apparatus as set forth in claim 1, wherein the constant current supply is configured to regulate an amount of the constant current which flows between said pair of sensor electrodes, wherein said decision unit is configured to decide that the change request has been made to enhance the detection response at the lean change time when the internal combustion engine is in a transient period of time in which a load on the internal combustion engine is increasing and when the internal combustion engine is in a high load steady state period of time in which the internal combustion engine is on a high load by such a load increasing, and wherein based on a result of decision of said decision unit, the current controller is configured to increase a response level in the transient period of time above that in said high load steady state period of time and to variably control the response level of the detection response as the output characteristic through regulation of the constant current by said constant current supply.

* * * * *